United States Patent [19]
Martinez-Miller et al.

[11] Patent Number: 6,103,875
[45] Date of Patent: Aug. 15, 2000

[54] ANTIFUNGAL COMPOUNDS FROM *PSEUDOMONAS VIRIDIFLAVA*

[75] Inventors: Concepcion Martinez-Miller; Roger V. Miller; Gary A. Strobel, all of Bozeman, Mont.

[73] Assignee: Pharmagenesis, Inc., Palo Alto, Calif.

[21] Appl. No.: 08/978,788

[22] Filed: Nov. 26, 1997

Related U.S. Application Data

[60] Provisional application No. 60/032,037, Nov. 26, 1996, and provisional application No. 60/041,762, Mar. 31, 1997.

[51] Int. Cl.$^7$ .................................................. C07K 2/00
[52] U.S. Cl. ............................................................ 530/359
[58] Field of Search ......................... 530/359; 435/71.1, 435/170, 874

[56] References Cited

U.S. PATENT DOCUMENTS

| | | | |
|---|---|---|---|
| 4,439,425 | 3/1984 | Tarcsay et al. | 424/177 |
| 5,385,884 | 1/1995 | Hammond et al. | 514/11 |

FOREIGN PATENT DOCUMENTS

WO9208357  5/1992  WIPO .

OTHER PUBLICATIONS

Miller et al., Journal of Applied Microbiology 84(6): 937–944 (Jun. 1998). Abstract.

Billing, Eve., "*Pseudomonas viridiflava*" (Burkholder,1930; Clara 1934), J. Appl. Bact. 33: 492–500 (1970).

Debono, Manuel., et al., "Semisynthetic Chemical Modification of the Antifungal Lipopeptide Echinocandin B (ECB): Structure–Activity Studies of the Lipophilic and Geometric Parameters of Polyarylated Acyl Analogs of ECB," J. Med. Chem. 38: 3271–3281 (1995).

Flamand, M.C., et al., "Production of syringotoxin and other bioactive peptides by *Pseudomonas fuscovaginae*," Physiological and Molecular Plant Pathology 48: 217–231 (1996).

Jones,J.B.,et al., "Fluorescence on Single–Carbon Sources for Separation of *Pseudomonas syringae* pv. *syringae, P. syringae* pv. tomato, and *P. viridiflava* on Tomato Transplants," Plant Disease 70: 151–153 (1986). Feb.

Katayama, N., et al., "Fosfadecin and Fosfocytocin New Nucleotide Antibiotics Produced by Bacteria," J. Antibiot. (Tokyo) 43 (3): 238–246 (1990). Mar.

Liao, Ching–Hsing, "Cloning of Pectate Lyase Gene pel from *Pseudomonas fluorescens* and Detection of Sequences Homologous to pel in *Pseudomonas viridiflava* and *Pseudomonas putida*," Journal of Bacteriology 173 (14): 4386–4393 (1991). Jul.

Mariano, R.L.R., and S.M. McCarter, "Epiphytic Survival of *Pseudomonas viridiflava* on Tomato and Selected Weed Species," Microb Ecol 26: 47–58 (1993).

Schroth, Milton N., et al., "Phytopathogenic Members of the Genus Pseudomonas" in *Phytopathogenic Bacteria*. ed. Starr, Mortimer P., Springer–Verlag, New York, pp. 701–718 (1983).

Smith, P.L., and R.J. Green,Jr., "Isolation and characterization of a fungiastic principle produced by bacteria," Canadian Journal of Microbiology 14: 1289–1296 (1968).

Wells, J.M., et al., "Identification of bacteria associated with postharvest diseases of fruits and vegetables by cellular fatty acid composition: an expert system for personal computers," Phytopathology 83 (4): 445–455 (1993).

Bartizal, K. et al., Antimicrobial Agents and Chemotherapy, vol. 36(8), p. 1648–1657, Aug. 1992.

Bartizal, K. et al., Antimicrobial Agents and Chemotherapy, vol. 39(5), p. 1070–1076, May 1995.

Schmatz, D.M. et al., The J. of Antibiotics, vol. 45(12), p. 1886–1891, Dec. 1992.

Balkovec, J.M. et al., J. Med. Chem., vol. 35(1), p. 194–198, 1992.

Debono, M. et al., ICAAC, vol. 33(0), p. 185, abstract #359, Oct. 1993.

Torres–Rodriguez, J.M. et al., Mycoses, vol. 32(6), p. 316–318, Jun. 1989.

Bouffard, F.A. et al., J. Med. Chem., vol. 37(2), p. 222–225, 1994.

Tang, J. et al., Antimicrobial Agents and Chemotherapy, vol. 35(1), p. 99–103, Jan. 1991.

Angiolella, L. et al., J. of Antimicrobial Chemotherapy, vol. 33(6), p. 1137–1146, 1994.

Kurtz, M.B. et al., Antimicrobial Agents and Chemotherapy, vol. 38(7), p. 1480–1489, Jul. 1994.

Hobbs, M. et al., Eur. J. of Clinical Microbiology Infectious Diseases, vol. 7(1), p. 77–81, Feb. 1988.

Richardson, M.D. et al., FEMS Microbiology Immunology, vol. 76(5), p. 299–303, Oct. 1991.

Meshulam, T. et al., J. of Antimicrobial Chemotherapy, vol. 24(5), p. 741–745, Nov. 1989.

Rennie, R.P. et al., Mycoses, vol. 32(3), p. 145–150, Mar. 1989.

*Primary Examiner*—Jean C. Witz
*Attorney, Agent, or Firm*—Susan T. Evans; LeeAnn Gorthey

[57] ABSTRACT

The present invention is directed to a family of unique antimycotic lipopeptide compounds produced by *Pseudomonas viridiflava*. The lipopeptides are effective against both human and plant fungal pathogens, and are typically characterized by their ability to inhibit growth of *Candida albicans*. Representative lipopeptides of the invention have molecular weights of 1137, 1153, 1164 and 1181 daltons.

14 Claims, 8 Drawing Sheets

Potential Acyl Groups for Semisynthetic Ecomycins
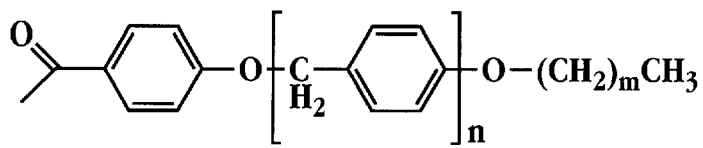
Generic Structure
where n = 0-3, m = 0-12
Building Blocks:
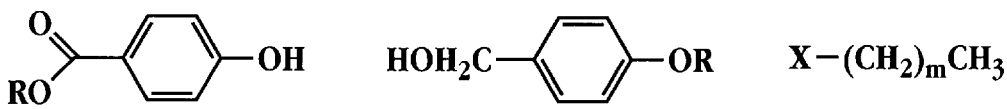
Key Sequence:
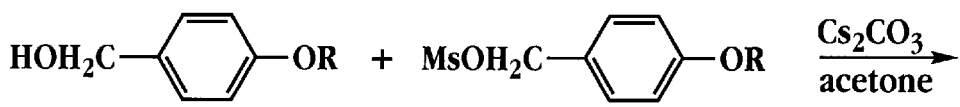
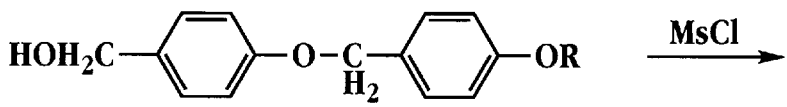
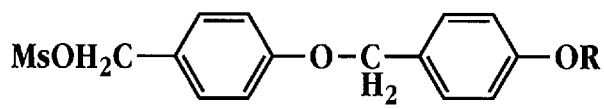
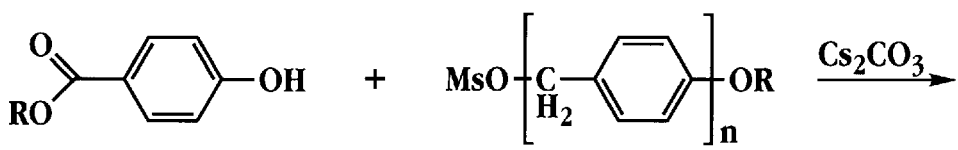
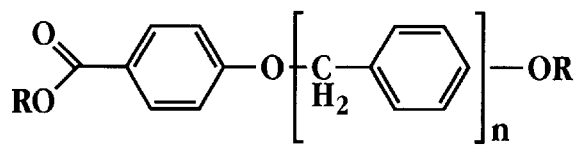
Fig. 8

ANTIFUNGAL COMPOUNDS FROM PSEUDOMONAS VIRIDIFLAVA

This application claims the benefit of U.S. Provisional Application No. 60/032,037, filed on Nov. 26, 1996, incorporated herein by reference in its entirety, and claims the benefit of U.S. Provisional Application No. 60/041,762, filed on Mar. 31, 1997, also incorporated herein by reference in its entirety.

FIELD OF THE INVENTION

The present invention relates to a family of unique antimycotic lipopeptide compounds produced by *P. viridiflava*, and to methods for treating fungal infections which employ these compounds.

REFERENCES

Ausubel, F. M., et al., in *CURRENT PROTOCOLS IN MOLECULAR BIOLOGY*, John Wiley and Sons, Inc., Media Pa. (1992).
Debono, M., et al., *J. Med. Chem.* 38:3271–3281
Galgiani, J. N., et al., *NCCLS DOCUMENT M27-P*, NCCLS, Villanova, Pa. (1992).
Gilman, A. G., et al., in *THE PHARMACOLOGICAL BASIS OF THERAPEUTICS*, Eighth Ed., Pergamon Press, New York, (1990).
Green, L., et al., *J. Immunol. Meth.* 70:257–268 (1984).
Gross, D. C., and DeVay, J. E., *Physiolog. Plant Pathol.* 11:13–28 (1977).
Gross, D. C., et al., *J. App. Bacteriol.* 43:453–463 (1977).
Hansch, C., et.al., *EXPLORING OSAR*, American Chemical Society, Washington, D.C., (1995).
Jones, J. B., *Plant Disease* 70(2):151–153.
King, E. O., et al., *J. Lab. & Clin. Med.* 44:302–307 (1954).
Klement, Z., et al., Eds., *METHODS IN PHYTOBACTERIOLOGY*, Budapest, Hungary, pp 67–96 (1990).
Lelliot, R. A., et al., *J. App. Bacteriology* 29:470–489 (1966).
Maniatis, T., et al., in *MOLECULAR CLONING: A LABORATORY MANUAL*, Cold Spring Harbor Laboratory Press, Cold Spring Harbor, N.Y. (1982).
Miller, J. H. in *A SHORT COURSE IN BACTERIAL GENETICS*, Cold Spring Harbor Laboratory Press, Cold Spring Harbor, N.Y. (1992).
*REMINGTON'S PHARMACEUTICAL SCIENCES* (1980)
Sambrook, J., et al., in *MOLECULAR CLONING: A LABORATORY MANUAL*, Vol. 2, Cold Spring Harbor Laboratory Press, Cold Spring Harbor, N.Y. (1989).
Schaad, N. W., Ed., *LABORATORY GUIDE FOR IDENTIFICATION OF PLANT PATHOGENIC BACTERIA*, 2nd Ed., APS Press, Minneapolis, Minn., pp. 23, 60–80 (1988).
Schroth, M. N., et al., in *SELECTIONS FROM THE PROKARYOTES, A HANDBOOK ON HABITATS, ISOLATION AND IDENTIFICATION OF BACTERIA*, (Starr, M. P., Ed.) Springer-Verlag, New York, N.Y., Chapter 60 (1983).
Stachelhaus, T., et al., *Science* 269:69–72 (1995).
Thomas, A. H. J., *Antimicrob. Chemother.* 17:269–279 (1986).
Turner, W. W., and Rodriguez, M. J., *Curr. Pharm. Des.* 2:209 (1996).
Wilkie, J. P., et al., *N. Zealand J. Agric. Res.* 16:315–323 (1973).

BACKGROUND OF THE INVENTION

Fungi are simple life forms such as molds, mildews, yeasts and mushrooms, with over 100,000 different species of fungi known to exist worldwide. Although most fungi are harmless, there a number of species that can cause illness and even fatal disease. The study of fungi and fungal diseases is referred to as mycology.

Fungi can cause various diseases and infections such as pulmonary candidiasis and blastomycosis. certain yeastlike organisms, e.g., *Cryptococcus neoformans*, may cause serious infections of the central nervous system. These fungal diseases are classified as "deep" fungal infections, which are those affecting the internal organs. Fungal infections may also be classified as superficial, which encompasses those affecting the skin, hair, nails, and genitals. Common superficial fungal infections include candidiasis (thrush), caused by the yeast *Candida albicans*, and tinea (including ringworm and athletes foot).

The incidence of opportunistic fungal infections in humans has steadily increased over the past several years. This is particularly true among patients whose immune systems have been compromised by conditions such as hematologic malignancy, myelosuppressive therapy, or HIV infection.

Fungal infections caused by Candida and Torulopsis have been reported in nearly 12 percent of leukemia patients following chemotherapy. Acute candidiasis has is currently on the rise, infecting up to five percent of newborns, five percent of all cancer patients, and ten percent of debilitated, elderly hospital patients. *Candida albicans* has become the fourth most common causal agent of sepsis in the United States, with a five-fold increased incidence during the decade of the 1980's, and mortality rates of 50 to 90 percent. The Centers for Disease Control (CDC) estimate that between 3 and 25 percent of patients with AIDS or AIDS related complex (ARC) will develop an opportunistic disease, with *Cryptococcus neoformans* constituting the fourth most common infection in these patients. Overall, over 30 percent of reported AIDS patients have had associated, potentially fatal, mycotic infections.

The incidence of non-*albicans* candidiasis, such as *C. kruzii* and *C. glabrata* is also increasing, possibly due to the emergence of organisms that are resistant to current antifungal therapies. Infections caused by species of Aspergillus, Fusarium, and Trichosporon, each associated with high mortality rates, are also increasing. Additionally, fungal species previously believed to be benign are beginning to appear as agents of previously unrecognized mycoses.

Even with the increase in the incidence of serious fungal infections, the number of current therapies available to counter these mycoses has been rather limited. Amphotericin B, developed in the 1950's, still remains the drug of choice for most fungal diseases, even though its toxicity causes undesirable side-effects including leucopenia, thrombocytopenia, renal tubular acidosis, hypokalemia, hypomagnesemia, headaches, nausea, and anemia (Thomas, 1986). Thus, a need exists for new antifungal compounds which are safe and effective in the treatment of fungal diseases.

Plants are also attacked by various fungi. Detrimental fungal plant pathogens include *Fusarium oxysporum*, which causes wilt in numerous plants, Sclerotinia sclerotiorum, which causes scelerotinia wilt, and *Rhizoctonia solani*, which can cause seedling damping off and root rot disease. Although most crops are treated with agricultural fungistats or fungicides, fungal damage to agricultural crops typically results in revenue losses to the agricultural industry of millions of dollars annually.

*Pseudomonas viridiflava* is a phytopathogenic bacterium associated with foliar, bud, flower, fruit, stem, or root diseases in a variety of plant species. Strains that are capable of producing necrotic and cankerlike lesions in plants have also been identified. Surprisingly, it has been discovered that certain novel lipopeptide compounds produced by *Pseudomonas viridiflava* possess potent antifungal properties.

SUMMARY OF THE INVENTION

The present direction is directed to a family of unique antimycotic lipopeptide compounds produced by *Pseudomonas viridiflava*. The lipopeptides inhibit growth of a number of different fungi, and are typically characterized by their capacity to inhibit growth of *Candida albicans*.

The lipopeptides of the invention are effective in inhibiting growth of both human and plant pathogenic fungi. The lipopeptides exhibit activity against human pathogenic fungi which include *Candida albicans, Candida glabrata, Candida parasilopsis*, and *Cryptococcus neoformans*. The lipopeptides are also active against plant pathogens such as *Alternaria solani, Diplodia viticola, Drechslera sorokiniana*, Fusarium spp., *Fusarium avenaceum, Fusarium lateritium, Fusarium oxysporum, Geotrichum citriaurantii, Rhizoctonia solani, Sclerotinia sclerotiorium, Sclerotium rolfsii* and *Stemphylium citri*.

The present invention also relates to strains of *P. viridiflava*, in substantially pure form, which are characterized by the following features: (i) the ability to produce a lipopeptide of the invention, (ii) fluorescence on King's B culture medium, (iii) an inability to produce acid from sucrose, (iv) an absence of oxidase and arginine dihydrolase activities, (v) an absence of levan formation in levan testing, (vi) a positive potato rot test, and (vii) a positive hypersensitivity in tobacco.

According to one aspect of the invention, the antifungal lipopeptides are produced by culturing, in a culture medium effective to support bacterial cell growth, a strain of *P. viridiflava*, and isolating from the culture medium, a lipopeptide of the invention.

In a related embodiment, a *P. viridiflava* lipopeptide having antifungal activity is produced by culturing, in a culture medium effective to support bacterial cell growth, a strain of *P. viridiflava* capable of inhibiting growth of Candida, followed by isolating one or more lipopeptides produced by the *P. viridiflava* strain from the culture medium. In one particular embodiment, the lipopeptides are isolated by (i) extracting lipopeptide present in the cell culture medium to produce a crude extract, (ii) separating the crude extract on a solid support to produce separated fractions, (iii) screening the separated fractions for antifungal activity, (iv) pooling the active fractions identified in (iii), and (v) purifying the pooled fractions. The pooled fractions may be purified by high performance liquid chromatography, organic extraction, liquid chromatography, or preparative thin layer chromatography.

According to one embodiment of the invention, the lipopeptide has a molecular weight between about 1 and 3 kD. Specific embodiments of the invention are directed to lipopeptides having molecular weights of 1137, 1153, 1164 and 1181 daltons, respectively.

According to yet another embodiment, a lipopeptide of the invention is characterized by having (i) a peptide segment including the amino acids 3-hydroxyaspartic acid, serine, threonine, homoserine, glycine, and alanine. In one particular embodiment, the lipopeptide also contains Asx (asparagine or aspartic acid), ornithine, and 2,4-diaminobutyric acid.

In another embodiment, the lipopeptide also contains, in addition to 3-hydroxyaspartic acid, serine, threonine, homoserine, glycine, and alanine, the amino acid Glx (glutamine or glutamic acid). A lipopeptide of the invention may also contain a fatty acid segment which includes palmitic acid.

In another aspect, the present invention provides a method of treating Candida infection in which a therapeutically effective amount of a lipopeptide of the invention is administered to a subject.

According to yet another aspect, the invention provides a method of treating Cryptococcus infection in which a therapeutically effective amount of a lipopeptide of the invention is administered to a subject.

The invention also provides a method of protecting a plant against fungal infection. In practicing one such method, infectable surfaces of a plant susceptible to fungal disease are coated with a *P. viridiflava* extract containing a lipopeptide of the invention.

In another aspect, the present invention is directed to an improvement in a method for treating a fungal infection in a host subject by administering amphotericin B. According to this aspect of the invention, a lipopeptide of the invention is administered in an amount effective to reduce the amount of amphotericin B required to effectively suppress the fungal infection by at least about 30% from the amount of amphotericin B required to achieve the same therapeutic effect in the absence of the lipopeptide.

BRIEF DESCRIPTION OF THE DRAWINGS

FIG. 8 presents reaction schemes for preparing a variety of exemplary synthetic lipid variants, where R=H or lower alkyl and X is a leaving group such as chloro, bromo, mesylate, etc.

DETAILED DESCRIPTION OF THE INVENTION

I. Definitions

Figure 1:
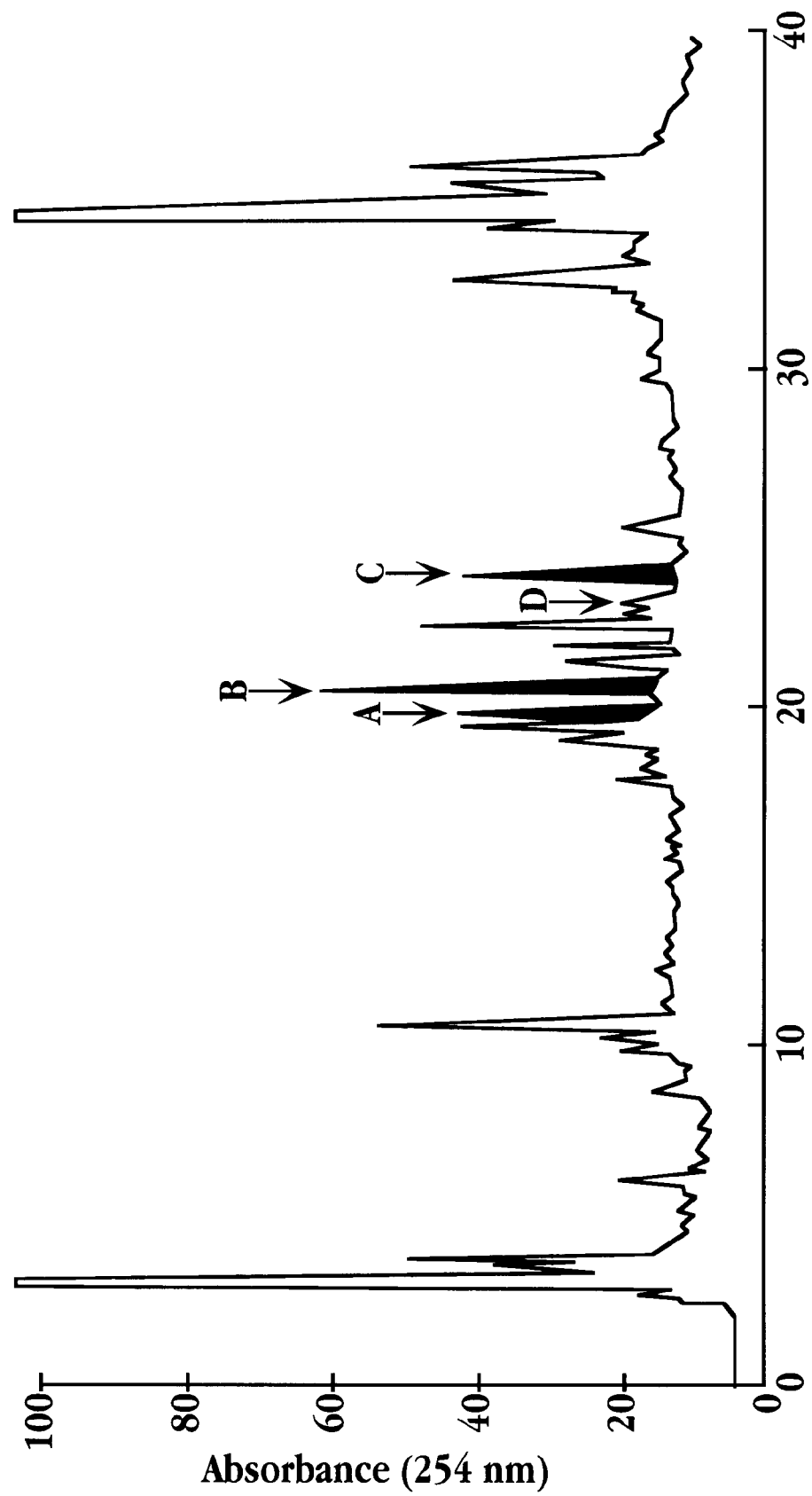
FIG. 1 is an HPLC elution pattern of a mixture of bioactive compounds from *P. viridiflava*. The arrows indicate peaks corresponding to the antimycotic compounds designated herein as Ecomycin A, B, C, and D.

As defined herein, a "purified lipopeptide" compound produced by *Pseudomonas viridiflava* is a lipopeptide that is at least partially purified away from unrelated or contaminating *Pseudomonas viridiflava* components (e.g., cells, cellular components, non-related or non-active proteins), or, for a synthetically produced lipopeptide, is separated from undesirable reaction side products. Methods and procedures for the isolation or purification of lipopeptides of interest are described herein (e.g., affinity purification, extraction). A purified lipopeptide may be a single bioactive lipopeptide, or composed of a mixture of lipopeptides capable of inhibiting fungal growth.

A "lipopeptide" as referred to herein is an organic compound composed of both a peptide portion and a fatty acid group. The peptide portion may be linear, cyclic, or branched, and may be composed of any of a number of different amino acid components, such as arginine, aspartic acid, 4-chlorothreonine, 2,4-diaminobutyric acid, glutamine, glycine, homoserine, 3-hydroxyaspartic acid, lysine, methionine, ornithine, serine and threonine. One representative lipopeptide, designated herein as Ecomycin A, possesses a peptide portion composed of 3-hydroxyaspartic acid, asparagine or aspartic acid (Asx), threonine, serine, homoserine, glycine, alanine, ornithine, and 2,4-diaminobutyric acid (Dab).

The fatty acid portion of the present lipopeptides may be branched or unbranched, and will typically have a chain length of about 10–18 carbon atoms. Exemplary fatty acid components include dodecanoic acid (lauric acid), tetradecanoic acid (myristic acid), hexadecanoic acid (palmitic acid), octadecenoic acid (stearic acid), oleic acid, linoleic acid, and linolenic acid. The fatty acid portion may be saturated or unsaturated. Two illustrative lipopeptide compounds of the present invention, Ecomycin A and Ecomycin B, appear to contain palmitic acid-derived lipid portions.

A lipopeptide compound of the invention, although produced by *Pseudomonas viridiflava*, may also be prepared by synthetic or recombinant techniques. Compounds produced by synthetic or recombinant methods may be identical to their naturally occurring counterparts, or may be analogs. An analog of a naturally occurring lipopeptide is one in which: (i) the lipophilic portion of the parent structure has been modified to contain a fatty acid side chain in which one or more methylene groups has been added, deleted, and/or functionalized to contain one or more substituents, such as an ether or a thioether functionality, or, to which one or more unsaturated bonds has been removed, introduced, or modified, such as by a deacylation/reacylation, and/or (ii) the peptide chain has been modified, such as by an insertion of one or more amino acids, a deletion of one or more amino acids, replacement of one amino acid with another, or by acylation of selective amino acid residues, and which possesses (iii) substantially the same or improved antifungal activity over its naturally occurring counterpart, (iv) a toxicity which is substantially the same or lowered from that of its naturally occurring counterpart, and (v) a linkage between the peptide and lipid portions which is chemically, enzymatically and metabolically stable. Exemplary linker groups include animal, amide, ether, carbamate, carbonate ester, thioether, and amino. Synthetic analogs of the present compounds are prepared by methods known in the art, such as those described in Debono (Debono, et al., 1995).

A lipopeptide of the invention also encompasses semi-synthetic compounds, that is, one in which a naturally-occurring peptide portion (i.e., a peptide component of a lipopeptide having antifungal activity produced by *Pseudomonas viridiflava*) is attached to a synthetic lipid moiety, or alternatively, a compound composed of a synthetic peptide portion attached to a naturally occurring lipid moiety (i.e., a lipid component of a lipopeptide having antifungal activity nd produced by *Pseudomonas viridiflava*). The peptide and lipid portions of such semi-synthetics are attached by a linker having the features described above.

A lipopeptide of the present invention, or a peptide portion thereof, may also be produced recombinantly, typically by employing a *Pseudomonas viridiflava* polynucleotide encoding a lipopeptide antifungal compound of the invention. A *Pseudomonas viridiflava* polynucleotide sequence encoding a lipopeptide will typically include post-translational modification signals for introducing the lipid moiety into the protein expression product. Alternatively, the lipid portion may be produced synthetically, e.g., by acylation of expressed protein.

A lipopeptide compound having antifungal activity is one which is effective to increase the mortality or inhibit the growth rate of fungi. Typically, a lipopeptide compound of the invention is one which is effective to produce a zone of inhibition of a given fungus at a concentration corresponding to less than about 100 $\mu$l/ml (the active lipopeptide may be in purified form, or, may be contained in an unpurified or semi-purified composition). For whole broth cultures, the strain of *P. viridiflava* is typically grown to approximately $1\times10^6$ to $6\times10^6$ CFU/ml. The zone or area of inhibition is typically measured 1–10 days after exposure.

By therapeutically effective amount is meant a concentration of active agent at the site of infection or in the bloodstream which is effective to inhibit fungal growth. This concentration can be determined from MIC values obtained from in vitro growth inhibition studies, using known human pathogenic fungi, and is related to the fungus type. Thus, for many applications, an effective dose is preferably one which results in a concentration of active antifungal compound in this range at the site of fungal infection.

The term fungus or fungi is meant to include a variety of nucleated, sporebearing organisms which are devoid of chlorophyll. Examples include yeasts, mildews, molds, rusts, and mushrooms.

"Antifungal" or "fungicidal" is the ability of a substance to increase the mortality or inhibit the growth rate of fungi as described above.

"Antibiotic" includes any substance which is able to inhibit or kill a microorganism.

"Whole broth culture" refers to a liquid culture containing cells and media. "Supernatant" refers to the liquid broth remaining when cells grown in the broth are removed, e.g., by centrifugation, filtration, etc.

"Lower alkyl" (in reference to FIG. 8) refers to an alkyl group containing from 1 to 5 carbon atoms, and may be straight chain or branched, as exemplified by methyl, ethyl, n-butyl, i-butyl, t-butyl.

II. Isolation and Identification of *P. viridiflava*

The present invention is based upon the discovery that certain strains of *Pseudomonas viridiflava*, a plant pathogenic bacterium, produce compounds which exhibit potent antifungal properties against a wide range of filamentous and non-filamentous fungi. The isolation and identification of *Pseudomonas viridiflava*, a naturally-occurring source of the active antifungal compounds of the invention, will now be described.

A. Sources of *P. viridiflava* and Preliminary Screening for Antimycotic Activity

*Pseudomonas viridiflava* belongs to a group of plant-associated fluorescent pseudomonads that is either weakly pathogenic of saprophytic (Lelliot, et al., 1966). A number of plant hosts of *P. viridiflava* have been identified (Wilkie, et al., 1973), including tomato, kiwi, lettuce, and dwarf bean. *Pseudomonas viridiflava* also has a proclivity for association with many grass species, all of which represent potential sources of isolates of *Pseudomonas viridiflava*. Wild grasses are a preferred source of *Pseudomonas viridiflava*, including grasses from California, Louisiana, Israel, Switzerland, New Zealand, England, Hungary, and Tunisia (e.g., Example 3, Table 2). Grasses with slight to severe chlorotic lesions on the leaf blade are also preferred.

Upon collecting a number of different plant tissue samples, the samples are typically washed with sterile water, soaked in phosphate buffered saline (PBS) solution, or surface sterilized, and then chopped up and streaked onto agar medium, typically with a wire loop. A number of different common agar media can be used, such as nutrient glucose agar (NDA; Difco, Detroit, Mich.), yeast extract-dextrose-calcium carbonate, nutrient-broth yeast extract agar (NBY), and Kings' medium B agar (KB), the recipes for which are provided in Schaad (Schaad, 1988, page 3).

Colonies will typically appear on the medium in about 1–5 days. These colonies are then assayed for antimycotic activity, to determine which colonies produce compounds having antifungal activity. Any of a number of preliminary screening assays can be employed to determine antimycotic activity for the colonies of bacteria. One such assay, referred to herein as a spot test or overlay test (Gross and DeVay, 1977), is conducted by overlaying a five-day old culture with a suspension of *Candida albicans*, and then examining the culture for areas in which growth of Candida is inhibited. This screening assay is described in Example 1B. Other fungi against which antifungal activity can be preliminarily assessed, such as by spot testing, include *Candida kefir, Candida krusei, Candida glabrata, Candida parasilopsis, Candida tropicalis, Cryptococcus neoformans, Alternaria solani, Diplodia viticola, Drechslera sorokiniana*, Fusarium spp. (Capsicum), *Fusarium avenaceum, Fusarium lateritium, Fusarium oxysporum, Geotrichum citri-aurantii, Rhizoctonia solani, Sclerotinia sclerotiorum, Sclerotium rolfsii, Stemphylium citri, Aspergillus niger, Cladosporium resinae*, and *Postia placenta*. Representative bacterial isolates collected and identified as having antimycotic activity include isolates EB-273, EB-274, and EB-227. The collection and antimycotic assessment of these exemplary strains are described in Examples 1A and 1B.

After identifying cultures active in spot tests, these bacteria are then further characterized. Isolates characterized as *Pseudomonas viridiflava* are those to which the present invention is directed. A number of diagnostic tests for identifying a bacterial isolate as *Pseudomonas viridiflava* are described below.

B. Features of *P. viridiflava*

Bacteria belonging to the species *Pseudomonas viridiflava* possess a number of characteristic features, which have been described in detail (Schroth, et al., 1983; Jones, 1986; Schaad, 1988). One distinctive and readily identifiable feature of *Pseudomonas viridiflava* is its production of yellow, green fluorescent pigments on some media devoid of iron, such as Kings' B medium. A diagnostic test for assessing fluorescent pigment formation of unknown bacteria is described in Example 2D.

The features described below typify those of isolates belonging to the bacterial species *P. viridiflava*. It will be understood that species of microorganisms have normal Gaussian distributions for any of a number of characteristic traits (e.g. carbon utilization, fatty acid makeup, etc.), and that the mean of the population characterizes the group. Thus, the features described below typify *P. viridiflava*, but are not intended to represent a strict recitation of features belonging to each and every *P. viridiflava* isolate.

1. LOPAT Testing

Returning now to diagnostic tests for identifying *P. viridiflava*, after identifying cultures which fluoresce on King's B medium, the bacteria are typically further delineated by LOPAT tests (Levan formation, Oxidase test, Potato rotting ability, Arginine dehydrolase production, and Tobacco hypersensitivity) (Schaad, 1988). In evaluating the results of LOPAT testing, bacteria potentially belonging to the species *P. viridiflava* will, on the whole, exhibit the following characteristics: negative levan test, negative oxidase test, positive potato rot test, negative arginine dihydrolase test, and positive hypersensitivity in tobacco. Secondary LOPAT characteristics of *P. viridiflava* include negative 2-ketogluconate production, negative egg yolk reaction, negative nitrate reaction, and negative acid from sucrose (Klement, et al., 1990). More than 95%, and typically, closer to 100% of bacterial isolates belonging to the species *P. viridiflava* will exhibit the above LOPAT test results.

2. Additional Diagnostic Tests

Bacteria possessing LOPAT test results matching those described above for *P. viridiflava* are then submitted to additional diagnostic tests for positive identification, according to conventional diagnostic test protocols common in the art, and as further described in Schaad (1988). Various representative diagnostic test results for identifying *P. viridiflava* are as follows (Schroth, et al., 1983), where (+) indicates product formation or substrate utilization, and (−) indicates the absence of product formation or absence of substrate utilization: pectate gel: the sinking of colonies on gel occurs within pH range of 4.6–8.5, beta glucosidase (+), adonitol (−), anthranilate (−), betaine (+), erythritol (+), homoserine (−), inositol (+), L-lactate (+), mannitol (+), quinate (+), sorbitol (+), D-tartrate (+), L-tartrate (−). Typically, at least about 50% of all strains of *P. viridiflava* will exhibit the features described above.

In one approach for determining the identity of an unknown bacterial strain, the bacteria is placed on a Biolog MicroPlate™ (Biolog, Hayward, Calif.), which provides a standardized microtest method using 95 different tests to identify a broad range of enteric, non-fermenting, Gram-negative bacteria. The microplate testing method examines the ability of bacteria to utilize or oxidize a preselected panel of different carbon sources, as described in *GN MICROPLATE INSTRUCTIONS FOR USE*, BIOLOG, Hayward, Calif. September 1993.

Briefly, in conducting the test, the unknown isolate is suspended in sterile saline, and the resulting cell suspension is inoculated into the MicroPlate, 150 $\mu$l per well. Wells start out colorless, and those containing a chemical that is oxidized by the bacteria turn a purple color, indicating a positive result. The test results, i.e., the pattern of purple wells, are then processed using the MICROLOG 3™ software program available through Biolog, Inc. (Hayward, Calif.), which automatically cross references the pattern to an extensive library of species to determine a suitable match.

Bacterial isolate EB-273 (species *P. viridiflava*) was deposited with the American Type Culture Collection (ATCC), 10801 University Boulevard, Manassas, Va. 20110-2209 an International Depository established under the Budapest Treaty. The deposit was accepted by the ATCC on Feb. 6, 1997, and assigned an ATCC designation 55929. Bacterial isolates EB-274 and EB-227, both identified as strains of *P. viridiflava*, have been deposited in the EcoPharm Culture Collection, Montana State University, Bozeman, Mont.

Test results for the representative bacterial isolates EB-273, EB-274, and EB-227, identified as *Pseudomonas viridiflava*, are described briefly below. Carbon utilization test results for bacterial isolate EB-273 are summarized in Example 2, Table 1. As was evident from the pattern of MicroPlate test results (not shown), where a blackened or grey box indicated a positive result and an unshaded or blank box indicated a negative result, bioactive *P. viridiflava* isolates of the invention (e.g., isolates EB-273 to EB-423, represented in columns 14 through 31) appear to characteristically utilize the following carbon sources: L-arabinose, D-arabitol, D-galactose, D-glucose, D-sorbitol, cis-aconitic acid, citric acid, D-galacturonic acid, D-gluconic acid, D-glucuronic acid, quinic acid, D-saccharic acid, succinic acid, L-alanine, L-asparagine, L-glutamic acid, L-aspartic acid, L-proline, L-serine, and glycerol, referred to herein as non-variable carbon sources. Carbon sources which are characteristically unutilized by the bioactive *P. viridiflava* isolates of the invention were indicated by a row of blank boxes, and include α-cyclodextrin, dextrin, glycogen, N-acetyl-D-galactosamine, etc.

In examining the pattern of MicroPlate test results, it was determined that the bioactive *P. viridiflava* isolates of the invention also exhibit variability in their utilization of about 29 different carbon sources including: Tween 40, Tween 80, i-erythritol, m-inositol, D-psicose, mono-methyl succinate, acetic acid, formic acid, D-galactonic acid lactone, D-glucosaminic acid, α-hydroxybutyric acid, α-ketobutyric acid, D,L-lactic acid, malonic acid, propionic acid, bromosuccinic acid, succinamic acid, glucuronamide, D-alanine, L-alanyl glycine, glycyl-L-glutamic acid, L-histidine, L-leucine, L-pyroglutamic acid, D-serine, L-threonine, γ-aminobutyric acid, inosine, and uridine, referred to herein as variable carbon sources.

Representative carbon utilization test results for bacterial isolate EB-273 are summarized in Example 2, Table 1. As provided therein, EB-273 was found to utilize the following carbon sources: trigonelline, L-tartrate, Tween 40, L-arabinose, D-glactonic acid, lactone, L-alanine, D-arabitol, D-glacturonic acid, L-asparagine, D-fructose, D-glucuronic acid, L-aspartic acid, D-galactose, D-glucosaminic acid, L-glutamic acid, inositol, a-hydroxybutyric acid, glycyl-1-glutamic acid, D-mannitol, a-Ketoglutaric acid, L-proline, psicose, D,L-lactic acid, L-pyroglutamic acid, D-sorbitol, propionic acid, L-serine, methyl pyruvate, quinic acid, inosine, mono-methyl succinate, saccharic acid, uridine, acetic acid, succinic acid, glycerol, Cis-aconitic acid, bromosuccinic acid, D-1-glycerol phosphate, citric acid, succinamic acid, and formic acid, and glucuronamide.

Thus, an unknown isolate is determined to be *Pseudomonas viridiflava* by having, overall, the features described above, most notably, fluorescence on King's B culture medium, the inability to produce acid from sucrose, induction of a hypersensitive reaction in tobacco, utilization of the above-described non-variable carbon sources, positive potato rot test, and an absence of oxidase and arginine dihydrolase activities.

As can be seen from Example 3, and in particular, Table 2, a large percentage of isolates identified as *P. viridiflava* were found to exhibit antimycotic activity. Referring to a sampling of *P. viridiflava* isolates from the United States, Israel, Tunisia, New Zealand, and Costa Rica, on average, over half of the samples (i.e., greater than 60%) were found to possess antifungal properties, as evidenced by activity against Candida.

To further characterize the isolates, such as by examining the biodiversity among various isolates of *P. viridiflava*, it may be desirable to utilize a three-dimensional genetic distance model which maps various phenotypic properties, and determines relative relationships amongst various strains (Schaad, 1988, page 67). As described in Example 12, over 40 antimycotic-producing *P. viridiflava* isolates were mapped on the basis of 29 variable carbon sources, as previously described, to determine their extent of similarity to sample EB-273 (semi-purified extract) and to one another.

Figure 7:
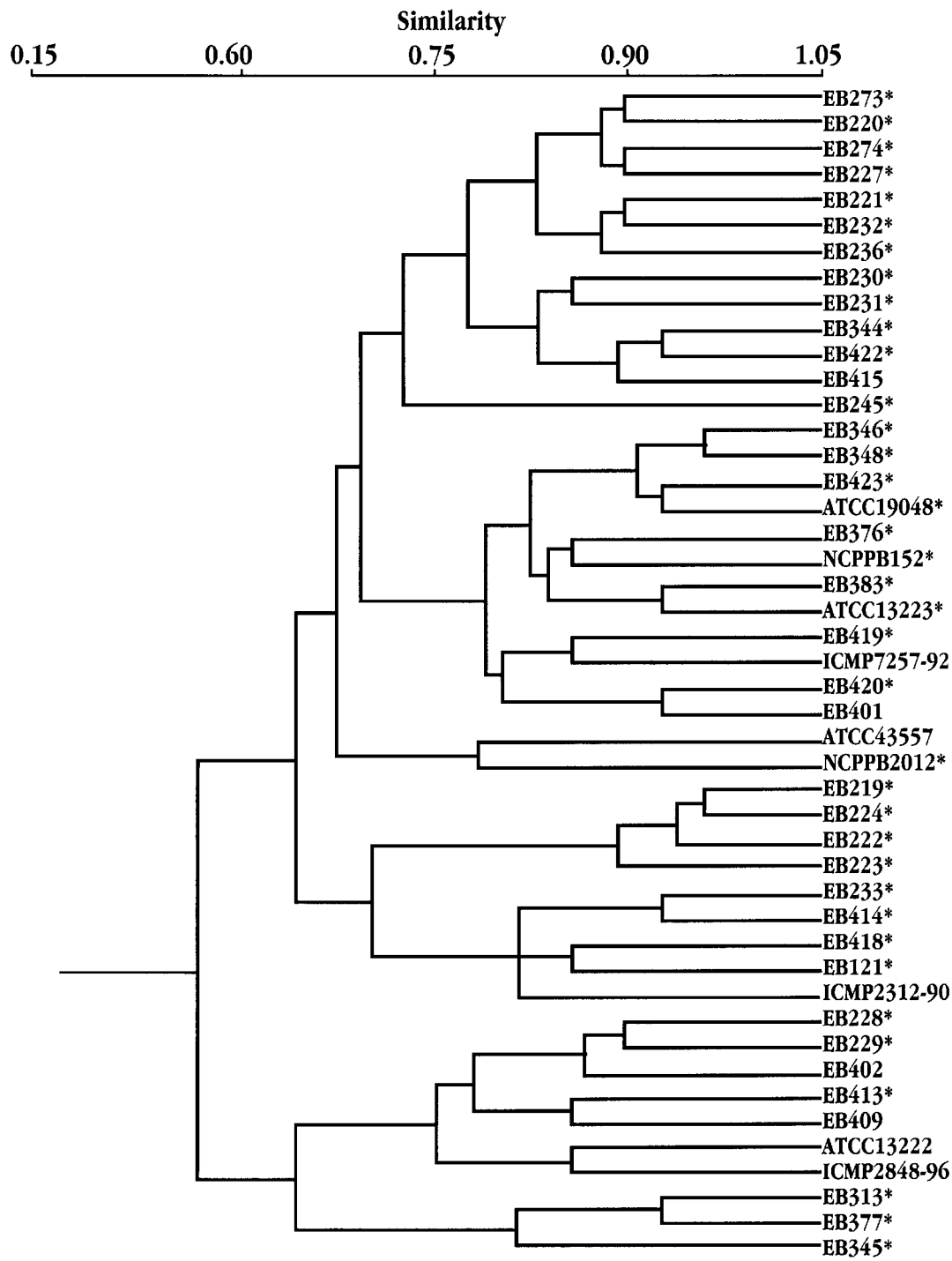
FIG. 7 is a dendogram of various *P. viridiflava* isolates, based upon variability in carbon source utilization.

Referring to the dendogram in FIG. 7, similarity amongst various isolates was assessed as follows. For the sake of illustration, using isolate EB-273 as a basis for comparison, and reading from right to left, isolate EB-273 was found to have the greatest similarity to isolate EB-220, as indicated by the vertical line connecting the two isolates, corresponding to a similarity index of about 0.90 or 90%. Similarity, as indicated by this one particular phenotypic marker (i.e., variable carbon source utilization) is determined from the value corresponding to a vertical line connecting two different isolates. For example, EB-273 shares a similarity of about 88% with isolates EB-274 and EB-227, which are about 90% similar to one another. Progressing down the dendogram, isolate EB-273 is about 66% similar to isolate EB-223, as evidenced by the vertical line connecting the two isolates, corresponding to a value of 0.66.

Based upon the information to date, it appears that the antimycotic *P. viridiflava* isolates of the invention will share a similarity index of at least about 0.50, where the similarity index is based on any of a number of phenotypic traits. Similarity index values relative to isolate EB-273, corresponding to the dendogram shown in FIG. 7, are provided in Table 8. Samples sharing high similarity indices can be grouped together as belonging to similar strains of *P. viridiflava*.

C. Isolation and Initial Characterization of Anti-Fungal Compounds Produced by *P. Viridiflava*

After identifying an isolate which (i) possesses antifungal activity, and (ii) is classified as *P. viridiflava*, the isolate is typically at least partially purified away from cellular components, to provide a supernatant or an extract having antifungal activity.

Typically, isolates are grown in potato dextrose broth, or Antibiotic Medium 3 (Difco Laboratories (Detroit, Mich.) as stationary cultures for a period of several days, followed by extraction with a suitable solvent such as acetone containing 0.1% trifluoroacetic acid. The resulting extract is then further separated by any of a number of common separation techniques, such as adsorption chromatography. Suitable solid support materials for chromatographic-based separations include Amberlite XAD-2 (Rhom & Haas). Recovered fractions are then assayed for antifungal activity, such as by spot testing as described previously. Fractions exhibiting activity are then pooled, and typically concentrated into dry form.

The resulting semi-purified antifungal preparation containing one or more active antifungal compounds may then be used directly for treating fungal infection, such as in topical applications (e.g., to inhibit fungal growth in plants), or alternatively, may be subjected to additional purification steps. Preparation of a semi-purified extract of isolate EB-273 is described in detail in Example 4.

The semi-purified antifungal *P. viridiflava* extract may be further purified by any of a number of commonly employed separation techniques, such as high performance liquid chromatography (HPLC), capillary zone electrophoresis (CZE), or counter current distribution. One preferred separation technique is HPLC. Column packing materials for use in chromatographic separations of this type include reverse phase supports (e.g., Altima C-18 column (Alltech Laboratories, Deerfield, Ill.)).

Typically, such HPLC separations are carried out using a gradient mixed solvent system. Exemplary solvents include acetonitrile, water, isopropanol, propanol, methanol, ethanol, with gradients typically ranging from 100% alcohol or a mixture of alcohol-water to 100% acetonitrile. The selection of a suitable solvent system and gradient will depend on a number of factors including the number of bioactive components contained in the semi-purified extract, the presence of additional organic components, column support material, flow rate, and the like, and will typically be determined experimentally.

As in the separation of a semi-purified extract, fractions are collected, assayed for the presence of organic compound, and assessed for bioactivity, typically by spot testing as previously described. Fractions exhibiting activity are then pooled, and typically concentrated into dry form. Concentrated samples are typically subjected to additional rounds of purification as needed. The purity and chemical identity of the recovered bioactive compounds is typically assessed by a number of commonly employed analytical techniques, such as by nuclear magnetic resonance spectroscopy NMR ($^{13}$C, $^1$H, using a variety of different pulse sequence experiments, including single and two dimensional NMR), mass spectroscopy, and amino acid-fatty acid analysis.

Isolation and characterization of four exemplary antifungal compounds from *Pseudomonas viridiflava* extract EB-273, referred to herein as Ecomycins A–D, are described in Examples 4–6. An HPLC trace of a mixture of bioactive compounds contained in semi-purified extract EB-273, prior to additional separation steps, is shown in FIG. 1. Under the HPLC conditions described in Example 4, Ecomycin A had a retention time of 19.6 minutes. An HPLC trace of purified Ecomycin A is presented in FIG. 2. The corresponding retention times of Ecomycins B–D were 20.4, 23.8 and 23.1 minutes, respectively.

On the basis of various analytical tests, the antifungal compounds of the present invention were found to be lipopeptides, the features of which will be described in greater detail below. The lipopeptide compounds, Ecomycins A–D, are believed to be archetypical of an entire family of lipopeptides from *Pseudomonas viridiflava* that have several structural and biological features in common, including potent antifungal activity. The characteristics of these four exemplary antimycotic *Pseudomonas viridiflava* lipopeptides are provided below.

D. Features of Ecomycins A–D

Upon obtaining the bioactive compounds Ecomycins A–D in substantially pure form, the compounds were characterized using a number of different analytical techniques. As stated above, the class of bioactive compounds of the invention are believed to share a number of different features. These compounds have been classified as lipopeptides, as supported by both amino acid and fatty acid analysis.

1. Molecular Weight

Figure 3:
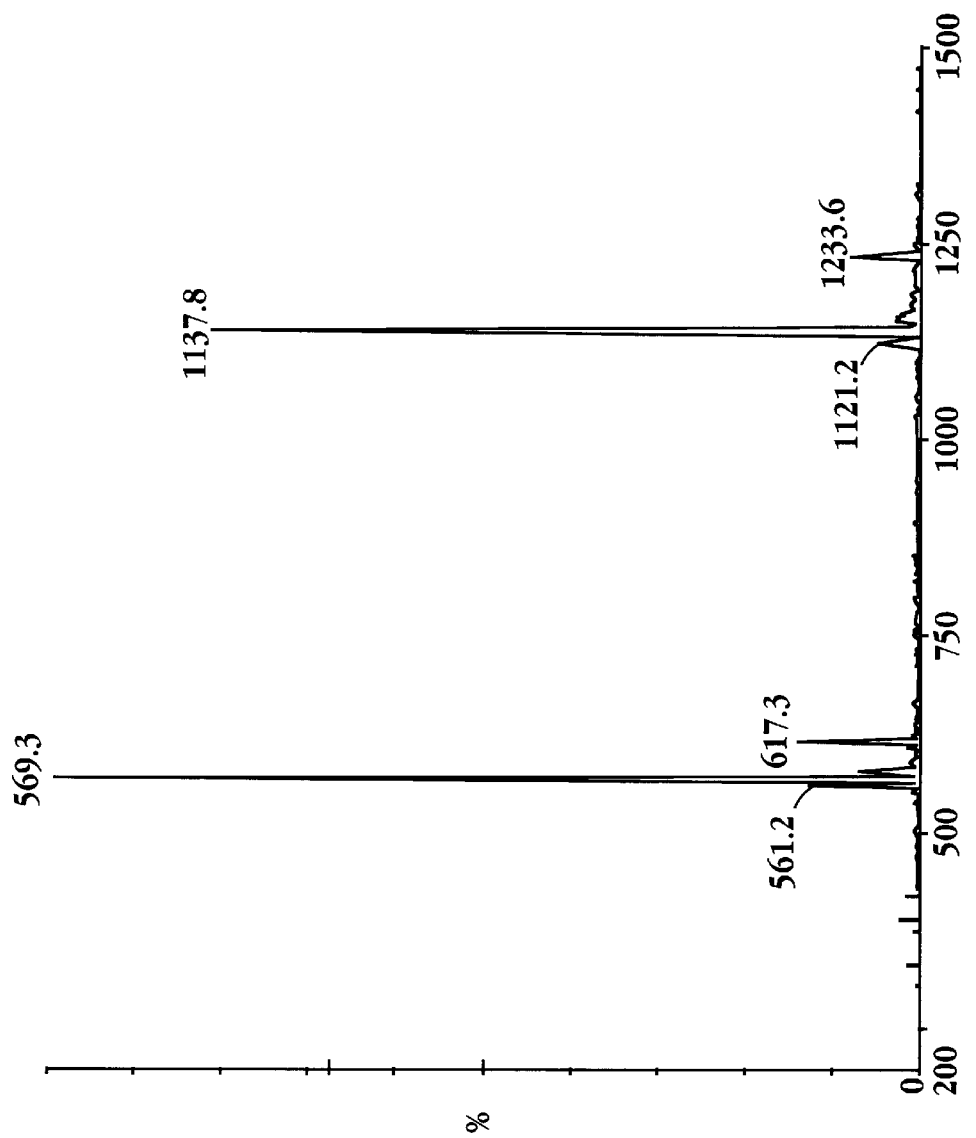
FIG. 3 is an electrospray mass spectrum of Ecomycin A.

The bioactive lipopeptide compounds characterized to date, i.e., Ecomycins A–D, were found to have molecular weights of 1137, 1153 1181, and 1164, respectively, as determined by mass spectroscopy. The mass spectral analysis of these compounds is described in Example 6. The results of an electrospray mass spectrum of Ecomycin A is presented in FIG. 3.

2. Amino Acid/Fatty Acid Composition

On the basis of amino acid analyses, Ecomycins A, B and C contain similar molar compositions of amino acids, as presented in Tables 3 and 4. Specifically, based upon the characterization data to date, Ecomycins A, B and C all appear to contain the following amino acids: 3-hydroxyaspartic acid, serine, threonine, homoserine, glycine, and alanine. The relative molar ratios of the individual amino acids are given in Table 4. Although the amino acid "dab" is referred to herein generically as 2,4-diaminobutyric acid, this amino acid component may be either 2,4-diaminobutyric acid, or its dehydrated form, dehydrodiaminobutyric acid, as these two amino acids are indistinguishable by the analysis method described in Example 5.

Preliminary data indicates that Ecomycin D also contains the amino acids, glycine and arginine. Based upon these findings, it appears that the antifungal lipopeptides of the present invention (i) belong to a unique class of lipopeptides produced by *Pseudomonas viridiflava*, and (ii) share a number of structural and chemical features, including similar peptide fragments.

The lipopeptides of the invention also possess a lipophilic fatty acid portion. The fatty acid portion of the present lipopeptides may be branched or unbranched, and will typically have a chain length of about 10–18 carbon atoms. Exemplary fatty acid components include dodecanoic acid (lauric acid), tetradecanoic acid (myristic acid), hexadecanoic acid (palmitic acid), octadecenoic acid (stearic acid), oleic acid, linoleic acid, and linolenic acid. The fatty acid portion may be saturated or unsaturated. Two illustrative lipopeptide compounds of the present invention, Ecomycin A and Ecomycin B, appear to contain at least one palmitic acid residue, a saturated, C-16 lipid. Results of the fatty acid analysis of Ecomycins A and B are presented in Table 3.

3. pH Stability

Figure 5:
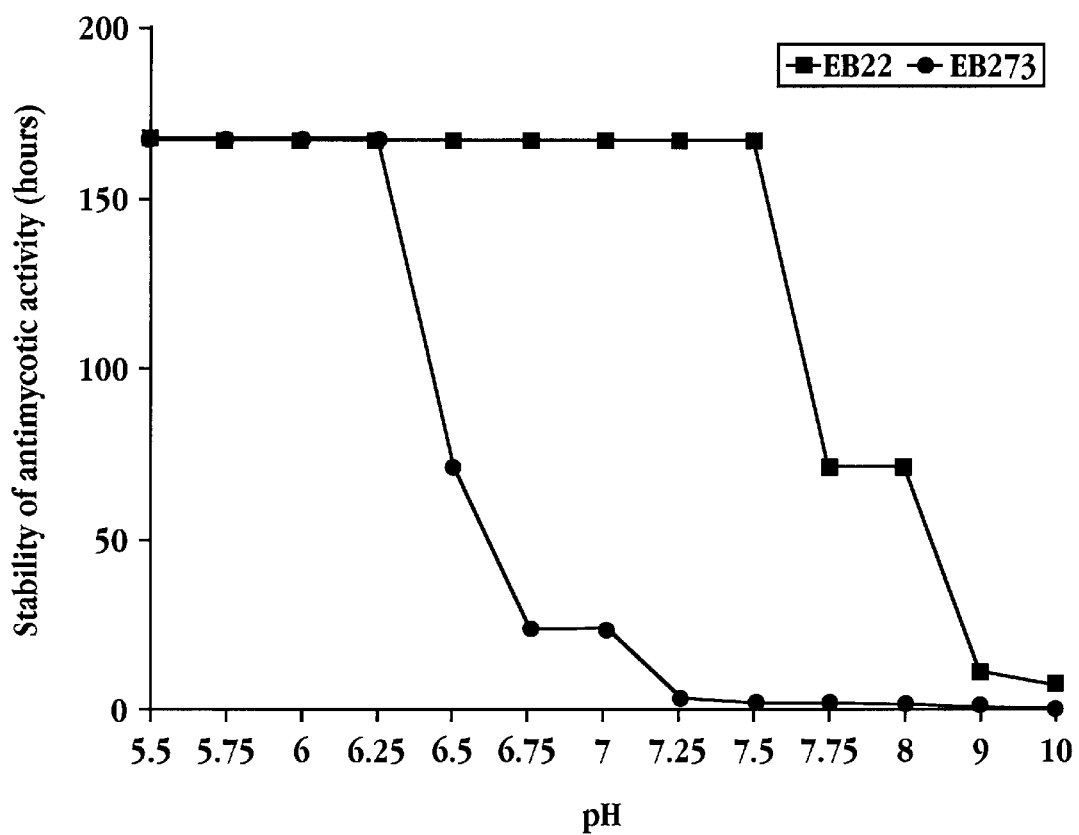
FIG. 5 is a plot illustrating the effect of pH as a function of activity against *Candida albicans* for (i) an extract of *P. viridiflava*, EB-273, and (ii) an extract of *P. syringae*, EB-22.

The lipopeptides of the invention are fairly stable under alkaline conditions, and appear to retain essentially one hundred percent of their antifungal activity up to pHs of at least about 7.25–7.5, for a period of at least about 7 days. As described in Example 10.B., semi-purified *Pseudomonas viridiflava* extract, EB-273, containing Ecomycins A–D, maintained its initial level of antifungal activity for an extended period of time (i.e., for over 3 days). Further, at pH 9, the semi-purified extract retained over 50% of its activity for up to about 12 hours. This feature of the lipopeptides of the invention, i.e., enhanced stability under basic conditions, is in contrast to that observed for bioactive bacterial extracts from *P. syringae*. As illustrated in FIG. 5, an extract of *P. syringae*, sample EB-20, rapidly degraded at a pH above about 6.25, and exhibited a complete loss of activity against *Candida albicans* at a pH above about 7.5. In contrast, at pH 7.5, sample EB-273 exhibited no observable loss of antifungal activity, indicating one unique feature of the present lipopeptides.

4. Solubility and Heat Sensitivity

The lipopeptides of the invention are soluble to an appreciable extent in solvents of varying polarities, such as water, methanol, acetone, isopropanol, and tetrahydrofuran, and somewhat soluble in solvents such as acetonitrile, chloroform and ethyl acetate. Results of solubility studies of *P. viridiflava* extract, EB-273, are provided in FIG. 4. Experimental details are provided in Example 10.A.

The lipopeptides of the present invention are also heat-resistant, i.e., they retain at least about 70% of their initial bioactivity for extended periods of time (i.e., several days) at temperatures ranging from about 4° to 60° C. Specifically, in an illustrative in vitro study, the stability of *P. viridiflava* extract EB-273, containing exemplary lipopeptides Ecomycins A, B, C, and D, was studied as a function of temperature. The details of this experiment are provided in Example 10C.

In briefly summarizing the results, at temperatures of 4° and 37° C., the antimycotic activity of extract EB-273 was retained at nearly 100 percent over the duration of the eight day study, in both liquid (dissolved) and solid form. At an elevated temperature of 60° C. for a period of 8 days, the samples retained partial activities ranging from 4% to 75% of their initial value, depending upon the form of the sample. The dry sample appeared to have the greatest stability under these conditions, maintaining approximately 75% of its initial activity.

Thus, the antimycotic lipopeptides of the present invention are (i) soluble in a variety of solvents, (ii) relatively stable (i.e., non-labile) under alkaline conditions, and (iii) stable over an extended range of temperatures, from about 4° C. to about 60° C.

E. Antifungal Properties of EB-273 and of Ecomycins A–D

The lipopeptides of the present invention, in both purified and semi-purified (i.e., *P. viridiflava* extracts) form, are effective in inhibiting growth of a variety of fungi, including Candida, Cryptococcus, Alternaria, Diplodia, Drechslera, Fusarium, Geotrichum, Rhizoctonia, Sclerotinia, Sclerotium, Stemphylium, Cladosporium, and Postia. Specifically, in illustrative overlay tests against a variety of pathogens, an exemplary *P. viridiflava* composition, *P. viridiflava* extract EB-273, containing Ecomycins A–D, inhibited growth of 21 different pathogenic strains of fungi. Specifically, as illustrated in Table 7 and described in Example 8, at concentrations of 100 μg/ml or less, EB-273 was effective in inhibiting growth of 6 different species of Candida, namely *Candida albicans, Candida kefir, Candida krusei, Candida glabrata, Candida parasilopsis*, and *Candida tropicalis*. Additionally, EB-273 was active against at least four different species of the plant pathogenic fungus, Fusarium, including Fusarium spp., *Fusarium avenaceum, Fusarium lateritium*, and *Fusarium oxysporum*. Other representative plant pathogenic fungi which displayed sensitivity to the lipopeptides of the present invention included *Cryptococcus neoformans, Alternaria solani, Diplodia viticola, Drechslera sorokiniana, Geotrichum citriaurantii, Rhizoctonia solani, Sclerotinia sclerotiorum, Sclerotium rolfsii*, and *Stemphylium citri*.

In addition to exhibiting antifungal activity against both human and fungal pathogens, the lipopeptides of the invention are also effective in inhibiting growth of fungi having a variety of other attributes. Three such classes of fungi, which display sensitivity to the lipopeptides of the invention, are Cladosporium, Postia, and Trichoderma, and more specifically, *Cladosporium resinae, Postia placenta* and Trichoderma spp., which cause degradation of fuel, degradation of wood, and mildew growth, respectively. Thus, the lipopeptides of the invention exhibit activity against a number of different types of fungi, including fungi responsible for (i) human mycoses, (ii) plant-related diseases, (iii) degradation of naturally occurring substances such as wood, (iv) degradation of processed materials such as jet fuel, and (v) household mildew.

The lipopeptides of present invention are highly efficacious, as evidenced by the minimum inhibitory concentrations (MIC) of both semi-purified and purified compositions of exemplary lipopeptides of the invention, in comparison to a known therapeutic antifungal agent, amphotericin B, against three different human pathogenic yeasts. The results of these illustrative MIC tests are presented in Example 7, Table 6. As illustrated in Table 6, the purified lipopeptides of the invention, and particularly Ecomycin A, possess a degree of potency similar to that of amphotericin A.

F. Recombinantly-Produced Ecomycins

Lipopeptides encompassed by the present invention may be synthetically produced, recovered from wild type isolates of *P. viridiflava*, produced recombinantly, and/or produced by a combination of any of the above approaches.

Genes encoding antimycotic lipopeptides produced by *P. viridiflava*, such as the exemplary lipopeptides, Ecomycins A–D, or precursors to these lipopeptides, are identified as follows.

The antifungal lipopeptides of the invention are typically first analyzed by CZE gel electrophoresis. The amount of antimycotic lipopeptides relative to the total amount of soluble protein can be determined, for example, by scanning densitometry. As a result of this determination (i.e., relatively high levels of lipopeptide production), purification and sequencing of peptide portions of the lipopeptides can be carried out, for example, by using a direct western blot approach.

In carrying out a western blot analysis, total proteins are western blotted to PDVF membrane and the regions corresponding to the lipopeptides of the invention are subjected to N-terminal amino acid sequence analysis to determine the corresponding amino terminal sequence corresponding to the lipopeptides.

A typical procedure for cloning a gene for Ecomycin A, a precursor of Eco A, or any of the lipopeptides of the invention, from cDNA synthesis to inverse PCR of a genomic copy of the gene, is as follows.

In carrying out the cloning procedure, mRNA for Ecomycin A is prepared by first extracting total RNA from the corresponding *P. viridiflava* isolate, i.e., EB-273, followed by precipitation and collection, according to standard protocols known in the art (Ausubel, et al., 1992). The isolation of mRNA from the total RNA is carried out, for example, using the "STRAIGHT A'S" mRNA isolation system (Novagen, Madison, Wis.) according to the manufacturer's instructions.

The mRNA obtained from the *P. viridiflava* isolate is then used as the template for cDNA synthesis, using primers such as dTRANDOM (synthesized by Operon Technologies, Inc., Alameda, Calif.). The resulting cDNA is subjected to a standard PCR (polymerase chain reaction) using primers corresponding to a portion of the dTRANDOM primer and a primer based on the lipopeptide amino terminal sequence, e.g., the amino terminal sequence of Ecomycin A.

The PCR amplification products are then analyzed. The resulting amplification products are agarose gel purified and subcloned into a suitable cloning vector such as Lambda ZAP II (containing a selectable marker gene) or Zap Express, containing the CMV promoter (Stratagene, La Jolla, Calif.). Subsequent sequence analysis of several of these clones allows identification of those clones whose sequence encodes a protein matching the amino terminal sequence of a lipopeptide of the invention, e.g., Ecomycin A.

In an alternative approach to cloning the gene for Ecomycin A, genomic DNA from *P. viridiflava* is used in a PCR reaction using primers internal to the cDNA sequence obtained as described above. This reaction produces a genomic clone of the Eco A gene containing most of the protein coding region.

The gene expression pattern of the Eco A gene, or any gene encoding a lipopeptide or lipopeptide precursor, can also be evaluated at the RNA and protein levels to confirm the expression, such as by Northern dot blots.

Once a gene encoding a lipopeptide or peptide precursor has been identified, hybrid genes encoding, e.g., Eco A derivatives, can be constructed. In one such approach, mutant strains of *P. viridiflava* are produced by chemical mutagenesis of a wild-type strain of *P. viridiflava* (e.g., with N-methyl-N-nitro-N'-nitrosoguanidine, ICR 170, or methane ethylsulfonic acid) according to standard protocols (Miller, 1992). Survivors of mutagenic treatment are then screened for antimycotic activity, as described previously.

Upon identification of antimycotic producing strains, southern blot experiments are used to evaluate the mutant DNA, and to identify DNA molecules having significant sequence identity (i.e., typically greater than 55%, more preferably greater than 80% identity using standard sequence comparison programs) with the Eco A gene, for example, to identify additional Eco A genes, or genes encoding a subject lipopeptide of the present invention.

Briefly, Eco A homologues are identified in a Southern blot of the genomic DNA of the chemically-induced *P. viridiflava* mutants. The mutant DNA is probed with a labelled DNA fragment containing the coding sequence of the Eco A gene. Alternatively, a probe can be made by isolating restriction-digest fragments containing the sequence of interest from plasmid DNA. Typically, the probe is labeled with a detectable moiety to enable subsequent identification of target molecules. Exemplary labeling moieties include radioactive nucleotides, such as $^{32}$P-labeled nucleotides, digoxygenin-labeled nucleotides, biotinylated nucleotides, and the like, available from commercial sources.

Target molecules are electrophoresed on a gel, blotted, and immobilized onto a nylon or nitrocellulose filter. Labeled probe molecules are then contacted with the target molecules under conditions favoring specific hybridization between the probe molecules and target molecules homologous to the probe molecules (Maniatis, et al., 1982; Sambrook, et al., 1989; Ausubel, et al., 1992).

Following contacting, hybridization, and washing, target molecules with sequences homologous to the probe are identified by detecting the label on the probe. The DNA containing the desired gene is then isolated and sequenced.

More often, a library of interest (e.g., genomic or cDNA) is screened with a probe containing sequences corresponding to the coding sequence of a known *P. viridiflava* lipopeptide encoding gene, such as the exemplary Eco A gene. The screening is performed using known methods (Ausubel, et al., 1992; Sambrook, et al., 1989), essentially as described above. Variants of identified genes of interest may also be generated by employing a targeted domain replacement method, such as that of Stachelhaus (Stachelhaus, et al., 1995).

G. Semisynthetic Analogs

A lipopeptide compound of the invention, although produced by *Pseudomonas viridiflava*, may also be prepared synthetically or semi-synthetically. Compounds produced by synthetic means may be identical to their naturally occurring counterparts, or may be derivatives.

Lipopeptide analogs encompass compounds in which (i) the lipophilic portion of the parent structure has been modified to contain a fatty acid side chain in which one or more methylene groups has been added, deleted, and/or functionalized to contain one or more substituents, such as an ether or a thioether functionality, or, to which one or more unsaturated bonds has been removed, introduced, or modified, such as by a deacylation/reacylation, and/or (ii) the peptide side chain has been modified, such as by an insertion of one or more amino acids, a deletion of one or more amino acids, replacement of one amino acid with another, or by acylation of selective amino acid residues.

Modification of a lipid side chain may be effected by a number of different approaches. In one approach, a deacylated intermediate is first prepared utilizing either a conventional chemical route, or by enzymatic hydrolysis. Microbes which may be used to remove the fatty acid portion of a lipopeptide include *Actinoplanes utahensis, Sclerotinia rolfsii, Fusarium solani*, and *Rhizoctina solani*. Exemplary reaction schemes for preparing a variety of synthetic lipid variants are illustrated in FIG. 8. As shown in FIG. 8, acyl derivatives that are somewhat rigid in structure and geometry are one class of preferred derivatives. Less flexible aryloyls have been correlated with reduced hemolysis in the echinochandins (Debono, et al., 1995).

Alternatively, semisynthetic analogs are prepared by derivatization of the natural product, based upon the amino acids present in the naturally occurring lipopeptide and their respective functional groups. One preferred method of preparing such semi-synthetic analogs is to directly acylate the natural product, e.g., by peracetylation with acetic anhydride. Alternatively, selective acylation of specific amino acid residues may be employed using any of a number of structurally diverse acylating agents known in the art.

Preferably, a lipopeptide analog will possess increased lipophilicity over the parent structure. One measure of a compound's lipophilicity is its octanol-water partition coefficient, expressed numerically as the log P value. Thus, preferred acylated lipopeptide derivatives are those having enhanced lipophilicity over the unmodified parent structure, as determined on the basis of the log P value, and more specifically, the clogP value.

To estimate clogP values, one can employ the CLOGP algorithm (Pomona College Medchem Software Manual, version 3, 1984), which performs log P calculations based upon the structural formula of the compound. The algorithm provides a clogP value which is an estimate of the log P of the entire molecule. In turning now to FIG. 4., one can estimate the clogP values for the native lipopeptides of the present invention. In looking at the solubility values along the left-hand axis, one can determine the corresponding log P values for the various ecomycin solvent extracts shown along the horizontal axis. Extracts possessing a solubility of less than or equal to 4 possess a clogP value less than about 0.5 (Hansch, et al., 1995), which suggests that the clogP values of the native lipopeptides are low, i.e., less than about 1.0. Thus, a preferred acylated derivative, that is, one having enhanced lipophilicity over the unmodified parent structure, will have a clogP value of greater than about 3.5. Additionally, any such derivative will preferably possess substantially the same or improved antifungal activity over its naturally occurring counterpart, while maintaining a toxicity which is substantially the same or lowered from that of its naturally occurring counterpart.

H. Cytotoxicity Studies

The lipopeptides of the present invention, in both semi-purified and purified form, are relatively non-toxic. In in vitro toxicity studies on cultured Jurkat human leukemia T cells and murine spleen cells (as described in Example 9), representative lipopeptide compositions, and the semi-purified extract EB-273 (containing Ecomycins A, B, C, and D), were found to be non-toxic up to the highest concentration tested, 12 $\mu$g/ml.

Thus, the lipopeptides of the invention, while possessing potent antifungal properties at concentrations used to assess cytotoxicity (e.g., Table 6), also appear to be non-toxic to both human and murine cells within this concentration range, as illustrated in Example 9.

I. Synergy with Amphotericin B

Turning now to another aspect of the present invention, the lipopeptides of the invention, when administered in combination with the known antifungal compound, amphotericin B, produce a synergistic interaction which is significantly enhanced over the fungal inhibitory effect of either the lipopeptides or amphotericin B alone, or as a result of an additive interaction between the two antifungal compounds and/or compositions.

Figure 6:
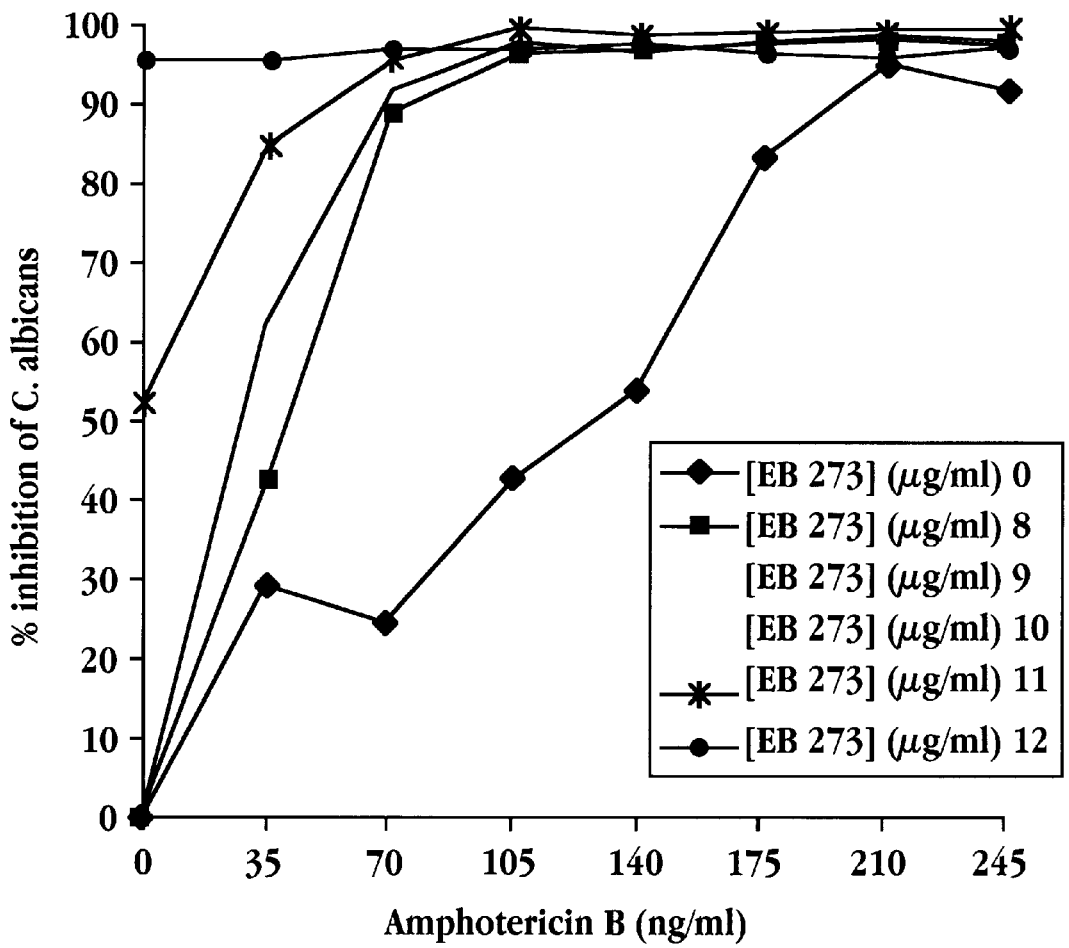
FIG. 6 is a plot illustrating a significant increase in inhibition of *Candida albicans* by Amphotericin B in the presence of varying amounts of an extract of *P. viridiflava*.

As described in Example 11 and further illustrated in FIG. 6, a composition containing the lipopeptides of the invention in combination with amphotericin B was shown to reduce the amount of amphotericin B required to effectively suppress growth of Candida by at least about 30% from the amount of amphotericin B required to achieve the same degree of inhibition in the absence of such a lipopeptides composition.

Briefly, in turning now to the illustrative experiments described in Example 11, varying amounts of amphotericin B were added to varying concentrations of an exemplary composition containing the antifungal lipopeptides of the present invention, extract EB-273, followed by a determination of the resulting inhibition of growth of *Candida albicans*.

As illustrated in FIG. 6, when employed as the sole bioactive agent, amphotericin B provided nearly complete inhibition of *C. albicans* at a concentration of 210 ng/ml, while at a concentrations of 35, 70, 105, 140, and 175 ng/ml, amphotericin B exhibited an inhibitory effect of approximately 30%, 25%, 43%, 55%, and 84%, respectively. That is, at a concentration of 70 ng/ml, amphotericin B had an inhibitory effect of only about 25% against Candida. However, at this same concentration (i.e., 70 ng/ml), the inhibitory effect of amphotericin B was enhanced to nearly 100% (i.e., nearly four-fold) by the addition of ecomycin extract EB-273 at concentrations from about 8–12 $\mu$g/ml or greater. At concentrations from about 8–10 $\mu$g/ml, extract EB-273 was ineffective at inhibiting growth of Candida when employed as the sole antifungal agent, illustrating an unexpected synergy between the lipopeptides of the invention and amphotericin B. At concentrations of 105 and 140 ng/ml amphotericin B, addition of extract EB-273 provided an approximate two-fold enhancement of activity against Candida over that exerted by amphotericin B alone. Further to the data presented in FIG. 6, isobolographic analyses utilizing a range of dosage responses confirmed that the interaction between amphotericin B and the ecomycin extract was synergistic rather than additive.

Referring now to FIG. 6, it can be seen that the concentration of amphotericin B required to achieve substantially complete inhibition of Candida is reduced by 16% (i.e., [210 ng/ml–175 ng/ml]/210×100), 33%, 50% and 66%, respectively, when employed in combination with a suitable concentration of exemplary lipopeptide extract EB-273.

Preferably, compositions of the present invention, when containing a combination of lipopeptide and amphotericin B, will contain a concentration of lipopeptide effective to reduce the amount of amphotericin B required to effectively suppress growth of Candida by at least about 30%, and preferably by about 50%, from that required to achieve the same degree of inhibition in the absence of lipopeptide.

Additional synergies are anticipated for the lipopeptides of the present invention. As an example, the ecomycins are believed to be 1,3-β-glucanase inhibitors. Thus, a composition containing one or more of the present lipopeptides in combination with a chitin synthase such as nikkomycin (from Streptomyces) may be expected to have potent (i.e., synergistically enhanced) in-vivo antifungal properties (Turner and Rodriguez, 1996).

J. Administration of Antifungal Lipopeptides

The main routes of compound delivery in the treatment method are oral, topical, and intravenous, as will be described below. Other drug-administration methods, such as subcutaneous injection, which are effective to deliver the active compound to a target site or to introduce the drug into the bloodstream, are also contemplated, and will depend upon the type of fungal infection to be treated and the likelihood of the development of drug resistance.

1. Pharmaceutical Compositions

Formulations containing the lipopeptide compounds of the invention may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like.

Preferably, the composition will be about 0.5% to 75% by weight of a lipopeptide compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

Liquid compositions can be prepared by dissolving or dispersing the active lipopeptide compound (about 0.5% to about 20%), and optional pharmaceutical adjuvants in a carrier, such as, for example, aqueous saline, aqueous dextrose, glycerol, ethanol and the like, to form a solution or suspension. The antifungal compounds may be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

Methods for preparing such dosage forms are known or will be apparent to those skilled in the art; for example, see *REMINGTON'S PHARMACEUTICAL SCIENCES* (1980). The composition to be administered will contain a quantity of the active lipopeptide compound(s) in a pharmaceutically effective amount for inhibiting fungal growth when administered in accordance with the teachings of this invention.

Formulations containing a lipopeptide of the invention may also contain amphotericin B, although the two antifungal compounds are not required to be administered in a single formulation. In situations in which the two compounds are delivered concurrently, i.e., in a single formulation, the formulation will typically comprise a colloidal preparation for intravenous or intrathecal administration, since amphotericin B cannot be given intramuscularly and is not adsorbed orally. In an alternative combination treatment regime, the two antifungal compounds are administered as discrete formulations. In utilizing this approach, amphotericin B is administered as described above, i.e., as a colloidal suspension, while the lipopeptide is typically administered orally or intravenously. Amphotericin B-lipopeptide combination therapy is typically used to treat mycoses such as those that are responsive to treatment with amphotericin B alone, such as histoplasmosis, blastomycosis, paracoccidioidomycosis, candidiasis, cryptococcosis, coccidioidomycosis, extraarticular sporotrichosis, aspergillosis, and mucormycosis.

Depending upon the mycosis to be treated and form of administration, when administered as the sole active agent, amphotericin B is typically administered over an 8–10 week period at a dosage of 0.4–0.6 mg/kg daily. In combination therapy with an antifungal lipopeptide of the present invention, the dosage of amphotericin will typically range from about 0.28–0.42 mg/kg daily. Preferably, the dosage of amphotericin B will be about 0.20–0.30 mg/kg daily, while the dosage of lipopeptide compound used in combination therapy will typically range from about 5–20 mg/kg daily.

2. Routes of Delivery

As described above, the main routes of drug delivery in the treatment method are oral, topical, and intravenous.

An injectable composition for parenteral administration will typically contain the antifungal lipopeptide compound in a suitable IV solution, such as sterile physiological salt solution. A dosage is selected to produce a target mid-range concentration in the bloodstream, according to known pharmacokinetic models (Gilman, et al., 1990). Dosages effective to achieve this range of concentrations in the blood in human patients can be readily determined from animal model studies, using known dose relationships between dose and pharmacokinetics between animal models and humans. For example, compound doses in the range of 0.10 to 10.0 $\mu$g/ml are generally effective for preventing fungal growth for a large number of types of fungi.

The antifungal compounds of the invention can also be delivered topically. For topical administration, a composition containing between 1–5% or more of an active lipopeptide is generally suitable. Regions for topical administration include the skin surface, eyes, and also mucous membrane tissues of the vagina, rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

3. Dosage Regime

During treatment of a fungal infection, the patient will typically receive periodic doses, e.g., from 3 times per week to daily doses of the drug, with the effectiveness of treatment being monitored according to standard symptom remission methods. The dosage requirements will vary with the particular drug composition employed, the route of administration, fungus type, and the particular subject being treated. Ideally, a patient to be treated by the present method will receive a pharmaceutically effective amount of lipopeptide compound in the maximum tolerated dose, generally no higher than that required before drug resistance develops.

K. Utility

The present invention relates to the discovery of lipopeptides produced by *P. viridiflava*, which are capable of inhibiting growth of a variety of fungi. Lipopeptides of the invention may be recovered from isolates of *P. viridiflava* (e.g., by the methods described herein) or, may be synthesized, by either synthetic or recombinant techniques. As demonstrated herein, the lipopeptides are potent antifungal agents, and can be utilized in semi-purified form (i.e., as *P. viridiflava* extracts) or, in purified form (e.g., Ecomycins A, B, C, and D).

Experiments performed in support of the invention demonstrate that the lipopeptides (i) are active against at least Candida, Cryptococcus, Alternaria, Diplodia, Drechslera, Fusarium, Geotrichum, Rhizoctonia, Sclerotinia, Sclerotium, Stemphylium, Cladosporium, and Postia, and (ii) are non-toxic, as shown in preliminary cytotoxicity assays.

The lipopeptides are useful in a variety of applications, as supported by the results of sensitivity assays. The lipopeptides can be used in therapeutic applications for treating mammalian mycoses. Experiments in support of the invention have demonstrated the lipopeptides to be effective in inhibiting growth of human pathogenic fungi such as *Candida albicans, Candida glabrata, Candida parasilopsis*, and *Cryptococcus neoformans*. Thus, the lipopeptides can be used to treat fungal infections of Candida and Cryptococcus.

The lipopeptides can also be used in combination therapy with amphotericin B for treating any of a number of fungal-related diseases known to respond to treatment with amphotericin B (e.g., histoplasmosis, blastomycosis, paracoccidioidomycosis, candidiasis, and cryptococcosis). The lipopeptides are effective in reducing the amount of amphotericin B required for administration, typically by at least about 30 to 50%. In so doing, the lipopeptides are useful in reducing or minimizing the toxic side-effects which often accompany administration of amphotericin B, when administered alone at its recommended dosage rate.

Alternatively, the lipopeptides can be used as additives in cosmetic or dermatological formulations for preventing fungal growth and/or product deterioration. The lipopeptides can be similarly employed in specialty and/or packaged foods, for prolonging shelf-life and preventing fungal contamination.

The lipopeptides also represent an important discovery in the agricultural area. Experiments conducted in support of the invention demonstrate that the subject lipopeptides are effective in inhibiting growth of plant pathogenic fungi which include *Alternaria solani, Diplodia viticola, Drechslera sorokiniana,* Fusarium spp., *Fusarium avenaceum, Fusarium lateritium, Fusarium oxysporum, Geotrichum citriaurantii, Rhizoctonia solani, Sclerotinia sclerotiorium, Sclerotium rolfsii* and *Stemphylium citri*. Thus, the lipopeptides can be used to treat plant diseases such as seedling damping off and root rot disease, or any disease caused by attack of one of the above fungal plant pathogens. The lipopeptides, in either pure or semi-purified form, can be used to coat infectable surfaces of a plant susceptible to fungal-promoted disease. For topical applications, the lipopeptides will typically be formulated either as a liquid (for spray applications), an aerosol, or powder (for dusting infectable plant surfaces). Alternatively, the lipopeptides may be used for systemic treatment of plant fungal diseases, for uptake by the root system. In such cases, the lipopeptides are typically formulated as granules, usually for convenience in application. Granule formulations are typically activated by application of water, and release of active compound typically occurs over an extended period of time, such as from 2–12 weeks.

The lipopeptides are also useful in industrial applications, such as in preventing fungal-promoted degradation of fuels (i.e., jet fuel). Experiments in support of the invention demonstrated the efficacy of the present lipopeptides in inhibiting growth of Cladosporium resinae, a fungus responsible for degradation of jet fuel. Thus, the lipopeptides can be used as "stabilizers" for preventing deterioration of substances susceptible to fungal-promoted degradation, such as wood.

Additionally, the lipopeptides of the invention can be used as additives in a number of household products, to prevent formation of mildew. For instance, the lipopeptides can be used as additives in paint, cleaning products, disinfectants, and the like.

The following examples illustrate, but in no way are intended to limit the present invention.

Materials and Methods

All fungi used for test purposes for sensitivity to the ecomycins were obtained from the ATCC or from the mycological collection at Montana State University, Bozeman, Mont.

EXAMPLE 1

A. Collection of Bacterial Strains of *P. viridiflava*

Grasses from several parts of the world were collected (e.g., as provided in column 1, Table 2 in Example 3 below), including various wild grasses growing in a grassland-hillside area west of Palo Alto, Calif. Preferred grass samples selected for bacterial isolation were those having slight to severe chlorotic lesions on the leaf blade.

The collected grass samples were placed between blotting papers. Within 48 hours of collection, leaf tissue samples were cut into 5 mm square pieces and soaked overnight in 0.1M sodium phosphate buffered saline solution (pH 6.8, 0.11M NaCl) at 4° C. After 12 hr, the samples were removed, placed at room temperature for 1 hr, and then streaked onto King's B, KB medium amended with cycloheximide. The semi-selective KB medium contained, on a per liter basis: 20 g protease peptone #3 (Difco Laboratories, Detroit, Mich.), 1.5 g $KH_2PO_4$, 1.5 g $MgSO_4.6H_2O$, 15 ml glycerol, 100 mg cycloheximide and 15 g agar (King, et al., 1954). In approximately 1–2 days, only 1 yellowish colony type appeared on the semi-selective plates. These yellowish colonies were then transferred to King's B plates and screened for antimycotic activity.

B. Identification of Isolates Exhibiting Antifungal Properties

The bacterial isolates were screened for antimycotic activity following a modified procedure of Gross (Gross, et al., 1977). Cells from each of the single colonies were spotted onto a potato dextrose agar (PDA) plate and allowed to grow for 5 days. The colonies were then removed with a sterile swab. The plate was exposed to chloroform vapors for 20 minutes, followed by dissipation of the chloroform vapors for an additional 30 min to kill remaining bacterial cells. To identify isolates possessing antifungal activity, the plate was oversprayed with a spore suspension of *Candida albicans*. The plate was then examined for areas in which growth of *C. albicans* was inhibited. Isolates identified as capable of inhibiting growth of *C. albicans* (isolates EB-273, EB-274 and EB-227) were then further characterized.

Bacterial isolate EB-273 (species *P. viridiflava*) was deposited with the American Type Culture Collection (ATCC), 12301 Parklawn Drive, Rockville, Md. 20852, USA, an International Depository established under the Budapest Treaty. The deposit was received by the ATCC on Feb. 6, 1997, and assigned an ATCC designation 55929. Bacterial isolates EB-274 and EB-227, both identified as strains of *P. viridiflava*, have been deposited in the EcoPharm Culture Collection, Montana State University, Bozeman, Mont., 59715.

EXAMPLE 2

Isolate Characterization and Species Identification

The isolates identified in Example 1 as having activity against *C. albicans* were further characterized using conventional methods for identifying plant pathogenic bacteria (Schaad, 1988).

A. Hypersensitive Reaction

The isolates were assayed for their ability to induce a hypersensitive reaction in tobacco according to the method of Schaad (Schaad, 1988, page 40). Approximately $10^9$ CFU/ml water of freshly cultured bacteria were pressure infused into the intercellular space of a leaf of tobacco, cv. "Burley" using a syringe. Within 24 hours, a complete collapse of tissue was noted, indicating a positive result.

B. Arginine Dehydrolase

The isolates were examined for their ability to grow under anaerobic conditions using the arginine dihydrolase enzyme system as described by Schaad (Schaad, 1988, page 69). Fresh cultures of the isolates were placed into test tubes containing Thornley's medium 2A (in g/l: peptone, 1.0; NaCl, 5.0; $K_2HPO_4$, 0.3; agar 3.0; phenol red, 0.01; arginine HCl, 10.0; adjusted to pH 7.2), plugged with melted agar, and incubated at 27° C. After 4 days, the samples failed to turn a red color, indicating a negative result.

C. Oxidase Test (Schaad, 1988, Page 23)

Cultures of the isolates were grown on nutrient agar supplemented with 1% glucose. After 24 hours, a small loop of the inoculum was rubbed on filter paper impregnated with 1% (w/v) aqueous tetramethyl-p-phenylenediamine dihydrochloride solution. After 60 seconds, it was noted that no purple color had developed, indicating that the strains were oxidase negative.

D. Fluorescent Pigment Formation

The isolates were tested for their ability to produce a fluorescent pigment on King's B medium according to the method of Schaad (Schaad, 1988, page 73).

Colonies of the isolates were grown on King's B Medium (King, et al., 1954) at 27° C. The colonies were then examined for fluorescence using a long wave (366 nm) ultraviolet lamp. The isolates fluoresced under these conditions, indicating production of fluorescein.

E. Carbon Source Utilization

Each of the bacterial isolates was tested for its ability to utilize or oxidize a preselected panel of 96 different carbon sources using the GN MICROPLATE™ test panel (Biolog, Hayward, Calif.), according to the manufacturer's recommended protocol (GN Microplate™, Instructions for Use, Biolog, Inc., Hayward, Calif., 1993). Wells in which no reaction occurred remained colorless; positive results were indicated by the appearance of a purple color. The test results were processed using the MICROLOG 3™ computer software program available through Biolog, Inc. (Hayward, Calif.), which automatically cross-references the pattern of purple wells to an extensive library of species.

A summary of the diagnostic test results for bacterial isolate EB-273 is presented in Table 1 below.

TABLE 1

| Test | Results |
|---|---|
| Hypersensitive reaction in tobacco | + |
| Arginine dehydrolase | − |
| Oxidase | − |
| Fluorescent on KB | + |
| Utilizes the following carbon sources: | | |

| | | |
|---|---|---|
| Trigonelline | L-Tartrate | Tween 40 |
| L-arabinose | D-glactonic acid lactone | L-alanine |
| D-arabitol | D-glacturonic acid | L-asparagine |
| D-fructose | D-glucuronic acid | L-aspartic acid |

TABLE 1-continued

| | | |
|---|---|---|
| D-galactose | D-glucosaminic acid | L-glutamic acid |
| m-inositol | α-Hydroxybutyric acid | Glycyl-1-glutamic acid |
| D-mannitol | α-Ketoglutaric acid | L-proline |
| Psicose | D,L-lactic acid | L-pyroglutamic acid |
| D-sorbitol | Propionic acid | L-serine |
| Methyl pyruvate | Quinic acid | Inosine |
| Mono-methyl succinate | Saccharic acid | Uridine |
| Acetic acid | Succinic acid | Glycerol |
| Cis-aconitic acid | Bromosuccinic acid | D-1-glycerol phosphate |
| Citric acid | Succinamic acid | |
| Formic acid | Glucuronamide | |

On the basis of the available data, including hypersensitivity on tobacco, fluorescence on King's B medium and carbon source utilization tests, isolates EB-273, EB-274 and EB-227 were each identified as antimycotic-producing strains of *Pseudomonas viridiflava*.

EXAMPLE 3

Screening Various Isolates of *P. viridiflava* for Antimycotic Activity

Bacterial isolates obtained from various sources (e.g., grasses, broadleaf plants and culture collections) and locales were screened for antimycotic activity as described in Example 1B above. A summary of the results is presented in Table 2 below.

TABLE 2

| | | Number of Isolates | | | |
|---|---|---|---|---|---|
| | | Produces Antimycotic | | No Antimycotic Activity | |
| Locality | Total | Grasses | Others | Grasses | Others |
| USA | 19 | 11 | 1 | 7 | 0 |
| Israel | 15 | 15 | 0 | 0 | 0 |
| Tunisia | 9 | 4 | 0 | 5 | 0 |
| New Zealand | 1 | 0 | 0 | 1 | 0 |
| Costa Rica | 1 | 0 | 1 | 0 | 0 |
| Standards | | | | | |
| ATCC (USA) | 2 | 0 | 1 | 0 | 1 |
| ATCC (Switzerland) | 2 | 0 | 1 | 0 | 1 |
| ICMP (New Zealand) | 3 | 0 | 0 | 0 | 3 |
| ICMP (Switzerland) | 1 | 0 | 0 | 0 | 1 |
| NCPPB (England) | 2 | 0 | 1 | 0 | 1 |
| NCPPB (Hungary) | 1 | 0 | 1 | 0 | 0 |
| NCPPB (Iran) | 1 | 0 | 0 | 0 | 1 |

As indicated by the screening results in Table 2, a large percentage of isolates identified as *P. viridiflava* were found to exhibit antimycotic activity. Referring to a sampling of *P. viridiflava* isolates from the United States, Israel, Tunisia, New Zealand, and Costa Rica, on average, over half of the samples (i.e., greater than 60%) were found to possess antimycotic activity. Antimycotic activity was indicated by the presence of a clear zone of inhibition around a 5 day old colony which had been killed with chloroform vapors prior to overlaying with a suspension of *Candida albicans*.

EXAMPLE 4

Ecomycin Purification

A. Isolation of Ecomycins A, B, and C

Cells from a single colony of EB-273 were used to inoculate 15 ml of potato dextrose broth and the culture was grown overnight with shaking at room temperature (23° C.). This culture was then used to inoculate 2800 ml flasks each containing 1000 ml of PD broth. The resulting cultures were grown for six days at 27° C. as still cultures. The entire culture fluid (with cells) was mixed with an equal volume of acetone, to which was added trifluoroacetic acid (TFA) to a final concentration of 0.1 percent. The acetone/culture mixture was left overnight at 4° C. Cells and debris were removed by centrifugation at 10,000×g for 20 minutes. The supernatant liquid was taken to dryness by flash evaporation at 50° C., and the residue resuspended in 1000 ml aqueous 1% TFA. This solution was then applied to an Amberlite XAD-2 column (20–60 mesh, 1×30 cm, Merck, Philadelphia, Pa.) that had been previously equilibrated with aqueous 0.1% TFA. The 1000 ml sample was loaded onto the column at the rate of 1 ml/min using a peristaltic pump. After loading, the column was washed successively with a column volume equivalent of $H_2O$/isopropanol 20:80 v/v, followed by two column volumes of 30:70 v/v $H_2O$/isopropanol with 0.1% TFA.

The bioactive compounds were then eluted with a linear gradient of 40% to 100% isopropanol with 0.1% TFA in water. Fractions (10 ml) were collected and bioactivity determined by spotting 20 μl of each fraction onto a 50% yeast/mannitol (Difco) agar plate. After drying, the plates were overlaid with *Candida albicans*. Fractions containing activity, as indicated by zones of inhibition of the *C. albicans*, were combined and then dried by flash evaporation. The dried residue was washed three times each with 15 ml of MeOH. The solution was filtered through a 0.45μ teflon filter and dried by flash evaporation. The semi-purified fraction was used in preliminary biological assay and characterization tests (described in detail below) and is referred to herein as the semi-purified Ecomycin preparation.

The semi-purified preparation (100 mg) was then further purified by HPLC on an Altima C-18 column (7.8 mm×250 mm, Alltech, Deerfield, Ill.) and eluted with a linear gradient of MeOH/$H_2O$ (1:1 v/v, 0.1% TFA) to acetonitrile/isopropanol (4:1 v/v, 0.1% TFA) over 35 minutes at a flow rate of 2 ml/min. The elution stream was monitored at 254 nm. Bioactivity was assessed by spotting a 20 ul sample from each fraction onto an agar plate containing yeast/mannitol agar medium (Difco dehydrated YM agar), overlaying the plate with a 0.4% suspension of *Candida albicans* in warm agar, and assessing each of the spots for zones of inhibition of *Candida albicans*. Bioactivity was noted in three of the fractions.

An HPLC trace of a mixture of the three bioactive fractions is presented in FIG. 1. Fractions which possessed bioactivity correspond to peaks having retention times of 19.6, 20.4, and 23.8 minutes.

Figure 2:
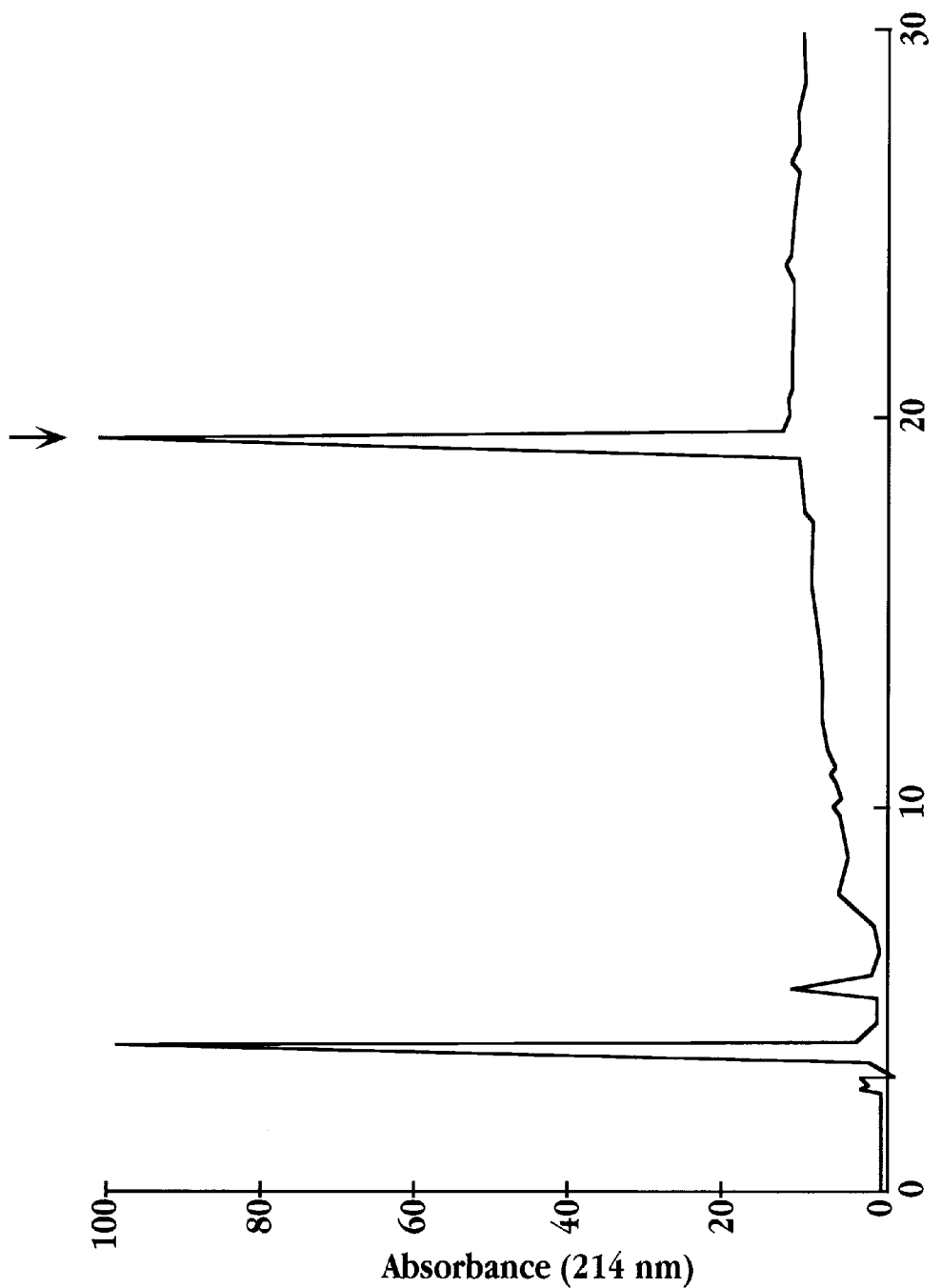
FIG. 2 is an HPLC elution pattern of purified Ecomycin A.

Those fractions containing bioactivity were rerun on the same column with a linear gradient of acetonitrile/$H_2O$ (1:3 v/v, 0.1% TFA) to acetonitrile/$H_2O$ (1:1 v/v, 0.1% TFA) at a flow rate of 3 ml/min over 25 minutes monitoring at 214 nm. Fractions were similarly assayed for sensitivity to *C. albicans*. FIG. 2 is an HPLC trace of a purified sample of the compound having a retention time of 19.6 minutes, referred to herein as Ecomycin A. Compounds having retention times of 20.4 and 23.8 minutes were similarly isolated, and are referred to herein as Ecomycins B and C, respectively.

A fourth compound, exhibiting activity against *C. albicans*, and having a retention time of 23.1 minutes, has also been identified, and is referred to herein as Ecomycin D.

The purity of the isolated ecomycins was also evaluated by thin layer chromatography (TLC) on Merck silica gel plates. Ninhydrin-positive spots were visualized for each of the samples.

A second TLC plate was allowed to dry overnight and overlaid with *C. albicans* in 0.4% agar containing 20 g/l glucose and 10 g/l yeast extract, and allowed to gel. The plate was incubated at 37° C. for several hours, followed by observation for zones of inhibition.

EXAMPLE 5

Amino Acid/Fatty Acid Analysis of Ecomycins

Lyophilized, HPLC-purified ecomycin samples were dissolved in methanol, placed in 6×50 mm glass tubes, dried in vacuo, and placed in a hydrolysis cylinder (Millipore, Bedford, Mass.). Approximately 300 µl of 6N HCl (Pierce Chemical Co., Rockford, Ill.) was added to the bottom of the vial, and the vial was then alternately purged with nitrogen followed by evacuation, three times prior to sealing under vacuum. Vapor phase hydrolysis was performed by heating at 110° C. for 22 hr. After cooling, the cylinders were dried in vacuo, opened, and the hydrolyzates were dissolved in 2% sodium citrate buffer (pH 2.0). The resulting samples were then analyzed using a Beckman Model 6300 Amino Acid Analyzer.

Moles of each amino acid were first determined using molar absorption values derived from amino acid standards. Integral values were determined manually based on the relative molar yields of the various amino acids. The amino acid/fatty acid test results for Ecomycin A, Ecomycin B, Ecomycin C, and Ecomycin D, and two known standards, syringotoxin and herbicolin B, are presented in Table 3. Relative molar amounts of amino acid components of Ecomycins A and B are presented in Table 4.

TABLE 3

| Peptide or Fatty Acid Component | Ecomycins A, B, and C | Ecomycin D (1164 Da.) | Syringotoxin (1136 Da.) | Herbicolin B (1137 Da.) |
|---|---|---|---|---|
| Arginine | | ✓ | | ✓ |
| Aspartic acid | | ✓ | | |
| 4-Chlorothreonine | | | ✓ | |
| 2,4,-Diaminobutric acid | | ✓ | ✓ | |
| Alanine | ✓ | | | |
| Glutamine | | | | ✓ |
| Glycine | ✓ | ✓ | ✓ | ✓ |
| Homoserine | ✓ | | ✓ | |
| 3-Hydroxyaspartic acid | ✓ | ✓ | ✓ | |
| Lysine | | ✓ | | |
| Methionine | | | | ✓ |
| Ornithine | | | ✓ | |
| Serine | ✓ | ✓ | ✓ | |
| Threonine | ✓ | ✓ | ✓ | ✓ |
| Fatty Acid | | | | |
| Myristic | | | ✓ | ✓ |
| Stearic | ? | ? | | |
| Palmitic | ✓ | ✓ | | |

TABLE 4

| Amino Acid | Ecomycin A | Ecomycin B | Ecomycin C |
|---|---|---|---|
| 3(OH)asp | 16.7 | 20.0 | 28.9 |
| Asx | 2.0 | 1.6 | ND |
| Threonine | 11.9 | 12.8 | 13.3 |
| Serine | 11.2 | 12.0 | 13.3 |
| Homoserine | 4.9 | 5.6 | 4.4 |
| Glx | ND | ND | 8.9 |
| Gly | 16.3 | 16.8 | 13.3 |
| Alanine | 7.5 | 17.6 | 6.7 |

TABLE 4-continued

| Amino Acid | Ecomycin A | Ecomycin B | Ecomycin C |
|---|---|---|---|
| Unknown | + | + | + |
| Ornithine | 13.8 | ND | ND |
| Dab | 15.8 | ND | ND |

Mole percents are presented as [(moles of each amino acid)/(moles of all amino acids)×100]. "ND" represents not detected, and "+" indicates the presence of an additional amino acid that was not quantifiable, due to the lack of availability of a corresponding standard.

EXAMPLE 6

Mass Spectral Analysis of Ecomycins A, B, C and D

Each of the purified ecomycins was subjected to electrospray mass spectroscopy. Samples were prepared by dissolving each of the ecomycins in methanol:water:acetic acid, 50:50:1 v/v/v. The samples were run on Montana State University's home-built instrument, using a spray flow of 2 µl min$^{-1}$ with a spray voltage of 2.2 KV via the loop injection method.

The electrospray spectrum yielded interpretable peaks of M+H$^+$ at 1138.3 and 569.4 (M+H+H)$^{2+}$ for Ecomycin A (FIG. 3), and 1154 and 577 for Ecomycin B. A summary of the mass spectroscopy results for Ecomycins A, B, and C is presented in Table 5 below. Ecomycin D was similarly determined to have a molecular weight of 1164 daltons.

TABLE 5

| Molecular Species | Ecomycin A | Ecomycin B | Ecomycin D | Ecomycin C |
|---|---|---|---|---|
| [M + M]$^+$ | 1138 | 1154 | 1165 | 1182 |
| [M+ M + M]$^{++}$ | 569 | 577 | 582 | 592 |
| Mass | 1137 | 1153 | 1164 | 1181 |

EXAMPLE 7

Minimal Inhibitory Concentration Testing (MIC) of Ecomycins

Samples of the semi-purified ecomycin preparation, purified Ecomycin A, and Ecomycin B were tested, along with a known antifungal compound, Amphotericin B, in a minimal inhibitory concentration test (MIC) modification of the NCCLS protocol (Galgiani, et al., 1995).

The results are presented below in Table 6.

TABLE 6

| | Minimal Inhibitory Concentration (µg/ml) | | | |
|---|---|---|---|---|
| Pathogenic Species (ATCC) | Semi-Purified Ecomycins | Ecomycin A | Ecomycin B | Amphotericin B |
| *Candida albicans* 90028 | 39 | 3.13 | 31 | 0.6 |
| *Candida albicans* 90029 | 20 | NT | 31 | 0.6 |
| *Candida glabrata* 90030 | 39 | NT | 8 | 0.6 |

TABLE 6-continued

Minimal Inhibitory Concentration (µg/ml)

| Pathogenic Species (ATCC) | Semi-Purified Ecomycins | Ecomycin A | Ecomycin B | Amphotericin B |
|---|---|---|---|---|
| Candida kefir 46764 | 16 | 1.5 | NT | 0.1 |
| Candida parasilopsis 90018 | 39 | NT | 4 | 0.1 |
| Cryptococcus neoformans 90012 | 19 | NT | 4 | 0.1 |
| Cryptococcus neoformans 90013 | 19 | NT | 4 | 0.3 |

NT = not tested

EXAMPLE 8

Sensitivity of Various Fungi to the Semi-Purified Ecomycin Preparation

Spot tests were performed using fungi from a variety of sources, to determine the sensitivity of these fungi to the semi-purified ecomycin preparation obtained in Example 4.4.

Spot tests for activity against *Candida albicans* were performed essentially as described in Example 1B. Fungi that were classified as sensitive to the semi-purified ecomycin preparation were those which exhibited sensitivity when exposed to concentrations of 100 µg/ml or less of the ecomycin preparation.

TABLE 7

| Organism | Attribute | Sensitivity |
|---|---|---|
| Aspergillus fumigatus | Pathogen | I |
| Candida albicans | Pathogen | S |
| Candida kefir | Pathogen | S |
| Candida krusei | Pathogen | S |
| Candida glabrata | Pathogen | S |
| Candida parasilopsis | Pathogen | S |
| Candida tropicalis | Pathogen | S |
| Cryptococcus neoformans | Pathogen | S |
| Alternaria solani | Plant Pathogen | S |
| Diplodia viticola | Plant Pathogen | S |
| Drechslera sorokiniana | Plant Pathogen | S |
| Fusarium spp. (Capsicum) | Plant Pathogen | S |
| Fusarium avenaceum | Plant Pathogen | S |
| Fusarium lateritium | Plant Pathogen | S |
| Fusarium oxysporum | Plant Pathogen | S |
| Geotrichum citri-aurantii | Plant Pathogen | S |
| Rhizoctonia solani | Plant Pathogen | S |
| Sclerotinia sclerotiorum | Plant Pathogen | S |
| Sclerotium rolfsii | Plant Pathogen | S |
| Stemphylium citri | Plant Pathogen | S |
| Aspergillus niger | Plastics Degradation (ATCC 9642) | I |
| Cladosporium resinae | Jet Fuel Degradation (ATCC 38834) | S |
| Postia placenta | Wood Degradation (ATCC 11538) | S |
| Trichoderma spp. | Mildew - Florida household | I |

As illustrated by the results in Table 7, the ecomycin preparation is effective in inhibiting growth of a variety of fungi, including Candida, Cryptococcus, Alternaria, Diplodia, Drechslera, Fusarium, Geotrichum, Rhizoctonia, Sclerotinia, Sclerotium, Stemphylium, Cladosporium, and Postia.

EXAMPLE 9

Cytotoxicity Studies

In vitro cytotoxicity tests were conducted on cultured Jurkat human leukemia T cells and murine spleen cells using serial dilutions of both the semi-purified ecomycin preparation and the purified compounds, Ecomycin A, Ecomycin B, and Ecomycin C. Assay results were determined using 3-(4,5-dimethylthiazol-2-yl)-2,5-diphenyltetrazolium bromide (MTT) according to the method of Green (Green, et al., 1984).

At concentrations up to the highest concentration tested, 12 µg/ml, the semi-purified ecomycin preparation was found to be non-toxic.

EXAMPLE 10

Solvent, pH, and Temperature Effect on Antimycotic Activity of Ecomycins

A. Solubility Testing

The solubility of the semi-purified ecomycin extract (EB-273) was assessed in a series of solvents ranging from most polar to least polar, on the basis of antimycotic activity of the residual solid.

Figure 4:
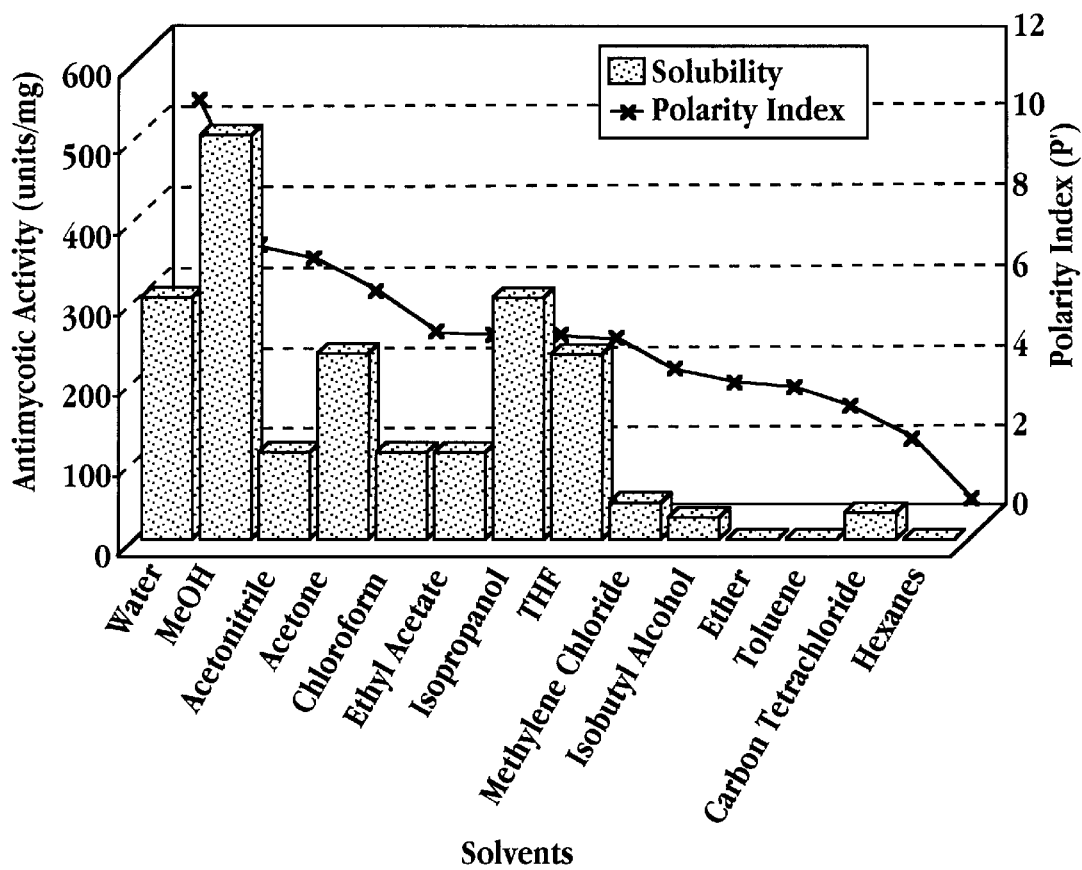
FIG. 4 is a bar graph illustrating the solubility characteristics of a semi-purified preparation of ecomycins (*P. viridiflava* EB-273 extract)

Tests were conducted as follows. To a sample of the semi-purified ecomycin extract (10 mg) was added a volume (200 µl) of solvent. The resulting mixture was agitated vigorously to aid in dissolution, and the soluble portion decanted from any undissolved solids. The extract was then placed in a laminar flow hood and the solvent was allowed to evaporate. The residual solid was redissolved in a number of serial dilutions, and the resulting solutions assessed by the spot test against *Candida albicans* as described previously. Decrease or loss in antimycotic activity was attributed to insolubility rather than to loss of activity. The results are shown in FIG. 4. As indicated in FIG. 4, the ecomycins are soluble to an appreciable extent in solvents of varying polarities, including water, methanol, acetone, isopropanol, and tetrahydrofuran (THF).

B. Stability of Ecomycins Versus pH

The effect of pH on the antimycotic activity of the semi-purified ecomycin extract, EB-273, was determined as follows.

The results are provided in FIG. 5. Results for an extract of *P. syringae* (extract EB-22), which produces pseudomycins, are shown for comparison. This study illustrates that at pHs up to about 7.5, the ecomycins retain their antifungal activity and remain active for an extended period of time. At pHs of about 7.5 or below, extract EB-273 retained its activity for the duration of the experiment, i.e., 7 days. At pHs from about 7.75 to 8, extract EB-273 maintained its initial level of activity for a period of at least 3 days, while at pH 9, the semi-purified extract remained active for up to about 12 hours.

C. The Effect of Temperature on Antimycotic Activity of Ecomycin Extract EB-273

The following samples of semi-purified EB-273 extract were prepared: (i) dry residue, (ii) dry residue dissolved in water, and (iii) dry residue dissolved in methanol. The various sample types were placed in sample tubes, capped and stored at temperatures of 4, 37, 60, and 100° C. Aliquots were withdrawn at 0.5, 1, 2, 3, and 8 days and assayed by serial dilution in spot tests as previously described.

At 4° or 37° C., antimycotic activities were retained at nearly 100 percent throughout the 8 day term of the study for all three sample types. At 100° C., antimycotic activity was lost within the initial 12 hours for both solid and liquid samples (water and methanol). After 8 days at 60° C., the dry sample retained over 75 percent of its initial activity, the methanol sample retained 42 percent of its activity, and the water sample retained 4 percent of its initial activity.

EXAMPLE 11

Synergy of Ecomycins with Amphotericin B

Experiments were conducted with the semi-purified preparation of ecomycins (extract EB-273), added individually or in combination with sub-fungicidal doses of Amphotericin B, to 96-well plates inoculated with *C. albicans*. The results are shown in FIG. 6.

As illustrated in FIG. 6, at a concentration of 210 ng/ml, amphotericin B provides nearly complete inhibition of *C. albicans*, while at a concentration of 70 ng/ml, Amphotericin B has an inhibitory effect of only about 25%. However, at this same concentration (i.e., 70 ng/ml), the inhibitory effect of Amphotericin B is enhanced to nearly 100% by the addition of the ecomycin extract at concentrations from about 8–12 µg/ml. Isobolographic analyses utilizing a range of dosage responses confirm that the interaction between Amphotericin B and the ecomycin extract is synergistic rather than additive.

EXAMPLE 12

Collection and Similarity Analysis of Additional Isolates Having Antifungal Properties Over 40 antimycotic-producing isolates have been collected and identified as *P. viridiflava*, as described in Examples 1 and 2 above. Based upon the isolates' utilization of 29 variable carbon sources, as described above), using BIOLOG™ GN 96-well microwell plates (as described in Example 2E), a numerical analysis was conducted to provide an indication of biodiversity amongst the isolate samples, and to determine the extent of similarity amongst various *P. viridiflava* isolates.

A dendogram was constructed from the results of the numerical analysis using the NTSYS-pc program from Exeter Software (Setauket, N.Y.), the results of which are presented in FIG. 7 and in Table 8 below. Similarity was measured as a function of an isolate's ability to utilize each of the 29 variable carbon sources described above, and is indicated along the horizontal axis.

Referring to the dendogram in FIG. 7, similarity amongst various isolates is assessed as follows. Using isolate EB-273 as a basis for comparison, and reading from right to left, isolate EB-273 shares about 90% similarity to isolate EB-220, as indicated by the value of the vertical line connecting the two isolates. Isolates EB-273 and EB-220 share about 88% similarity to isolates EB-274 and EB-227, which share about 90% similarity to one another. Samples sharing high similarity indices can be grouped together as isolates belonging to similar strains of *P. viridiflava*.

All bioactive bacterial isolates identified herein as belonging to the species *P. viridiflava* (e.g., those isolates contained in FIG. 7) have been deposited in the EcoPharm Culture Collection, Montana State University, Bozeman, Mont.

TABLE 8

| Isolate | Origin | Similarity to EB273 | TLC Rf(s) |
| --- | --- | --- | --- |
| EB273 | Grass, California | 1.00 | 0.47 to 0.48 |
| EB221 | Grass, Israel | 0.83 | 0.46, 0.52 |
| EB223 | Grass, Israel | 0.66 | 0.47 |
| EB227 | Grass, Israel | 0.88 | 0.46, 0.53 |
| EB228 | Grass, Israel | 0.58 | 0.46 |
| EB274 | Lilac, California | 0.88 | 0.47, 0.52, 0.63 |
| EB348 | Grass, Tunisia | 0.70 | 0.50 |
| EB413 | Grass, California | 0.58 | 0.47 |
| EB418 | Grass, California | 0.66 | 0.47 |
| ATCC 19048 | Lettuce, Louisiana | 0.70 | 0.46 |
| ATCC 13223 | Bean, Switzerland | 0.70 | 0.48 |

TABLE 8-continued

| Isolate | Origin | Similarity to EB273 | TLC Rf(s) |
| --- | --- | --- | --- |
| NCPPB 152 | Lettuce, England | 0.70 | 0.49, 0.53 |
| NCPPB 2012 | Bean, Iran | 0.69 | 0.53 |

[1]Isolates having ATCC designations were obtained from the American Type Culture Collection, Rockville, Maryland, USA. Isolates having NCPPB designations were obtained from the National Collection of Plant Pathogenic Bacteria, Harponden, Herts, United Kingdom.
[2]Similarity index to EB273 from dendogram (range 0.58–1.00).

The isolates were further characterized by thin layer chromatography, TLC. The similarities in $R_f$ values obtained for the various isolates shown in Table 8 and in FIG. 7 indicate that the active components are most likely chemically and structurally similar to the active lipoprotein components of isolate EB-273.

EXAMPLE 13

Characterization of Isolate EB-227

Isolate EB-227 was collected, screened for antimycotic activity, and characterized as described in Examples 1, 2 and 4 for isolate EB-273. Based upon the results of these tests, including HPLC profiles and mass spectral data, *P. viridiflava* isolate EB-227 has been characterized as producing ecomycins identical to Ecomycins A, B, and C described above.

While the invention has been described with reference to specific methods and embodiments, it will be appreciated that various modifications and changes may be made without departing from the invention.

What is claimed is:

1. A purified lipopeptide produced by *Pseudomonas viridiflava* which is effective to inhibit growth of *Candida albicans*, wherein said lipopeptide:
   (i) has a molecular weight of about 1153 daltons and contains a peptide segment which comprises 3-hydroxyaspartic acid, serine, threonine, homoserine, glycine, alanine, and Asx;
   (ii) has a molecular weight of about 1181 daltons and contains a peptide segment comprising 3-hydroxyaspartic acid, serine, threonine, homoserine, glycine, alanine, and Glx; or
   (iii) has a molecular weight of about 1164 daltons and contains a peptide segment comprising 3-hydroxyaspartic acid, serine, threonine, and glycine.

2. The lipopeptide of claim 1, produced by culturing, in a culture medium effective to support bacterial cell growth, a strain of *P. viridiflava*, and isolating from the culture medium, said lipopeptide.

3. The lipopeptide of claim 1, produced by culturing, in a culture medium effective to support bacterial cell growth, *P. viridiflava* strain ATCC No. 55929, and isolating from the cultured medium, said lipopeptide.

4. The lipopeptide of claim 1, wherein said lipopeptide contains a fatty acid segment having a chain length of about 10–18 carbon atoms.

5. A purified lipopeptide produced by *Pseudomonas viridiflava* strain ATCC No. 55929 wherein said lipopeptide:
   (i) has a molecular weight of about 1153 daltons and contains a peptide segment which comprises 3-hydroxyaspartic acid, serine, threonine, homoserine, glycine, alanine, and Asx;
   (ii) has a molecular weight of about 1181 daltons and contains a peptide segment comprising 3-hydroxyaspartic acid, serine, threonine, homoserine, glycine, alanine, and Glx; or (iii) has a molecular weight of about 1164 daltons and contains a peptide segment comprising 3-hydroxyaspartic acid, serine, threonine, and glycine.

6. An acylated derivative of a lipopeptide of claim 1, wherein said acylated derivative has (i) a clogP value greater than about 3.5 and (ii) is effective to inhibit growth of *Candida albicans*.

7. An antifungal composition comprising a lipopeptide of claim 1 and a pharmaceutically acceptable carrier.

8. A method of treating or protecting against a fungal infection, comprising administering to a subject, a therapeutically effective amount of a lipopeptide of claim 1.

9. A method of claim 8, wherein said fungal infection is selected from the group consisting of *Candida albicans, Candida glabrata, Candida parasilopsis*, and *Cryptococcus neoformans*.

10. A method of protecting a plant against fungal infection comprising:

applying to a plant or its environment a fungal-protecting amount of the composition of claim 7.

11. The method of claim 10, wherein said fungal infection is selected from the group consisting of *Alternaria solani, Diplodia viticola, Drechslera sorokiniana*, Fusarium spp., *Fusarium avenaceum, Fusarium lateritium, Fusarium oxysporum, Geotrichum citriaurantii, Rhizoctonia solani, Sclerotinia sclerotiorium, Sclerotium rolfsii* and *Stemphylium citri*.

12. The method of claim 10, wherein said composition is applied by coating infectable surfaces of the plant with said composition.

13. In a method of treating a fungal infection in a host subject by administering amphotericin B to the subject, the improvement comprising:

administering to the subject, a lipopeptide of claim 1, in an amount of lipoprotein effective to reduce the amount of amphotericin B required to effectively suppress the fungal infection by at least about 30% from the amount of amphotericin B required to achieve the same therapeutic effect in the absence of said lipopeptide.

14. The lipopeptide of claim 4, wherein said fatty acid segment is a palmitic acid residue.

* * * * *